(12) United States Patent
Ishikawa et al.

(10) Patent No.: US 6,447,448 B1
(45) Date of Patent: Sep. 10, 2002

(54) MINIATURE IMPLANTED ORTHOPEDIC SENSORS

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/475,820

(22) Filed: Dec. 30, 1999

Related U.S. Application Data

(60) Provisional application No. 60/114,400, filed on Dec. 31, 1998.

(51) Int. Cl.[7] .......................... A61B 5/00; A61B 19/00; A61B 5/04
(52) U.S. Cl. ................. 600/300; 600/373; 600/377; 128/899
(58) Field of Search ................. 128/899, 897, 128/903; 600/345, 300, 301, 372, 373, 377, 393

(56) References Cited

U.S. PATENT DOCUMENTS

| | | | |
|---|---|---|---|
| 3,944,982 A | 3/1976 | Mogi et al. .................. 340/171 |
| 4,333,072 A | 6/1982 | Beigel .................... 340/825.54 |
| 4,345,253 A | 8/1982 | Hoover ........................ 343/6.8 |
| 4,530,974 A | 7/1985 | Munro et al. ............. 525/329.4 |
| 4,618,844 A | 10/1986 | Takahashi et al. .............. 338/2 |
| 4,665,610 A | 5/1987 | Barth .......................... 29/580 |
| 4,754,314 A | 6/1988 | Scott et al. .................... 357/42 |
| 4,857,893 A | 8/1989 | Carroll ........................ 340/572 |
| 5,017,670 A | 5/1991 | Frautschi et al. ............ 527/313 |
| 5,197,488 A | * 3/1993 | Kovacevic ................... 600/595 |
| 5,312,439 A | * 5/1994 | Loeb ............................. 607/2 |
| 5,347,263 A | 9/1994 | Carroll et al. ............... 340/572 |
| 5,405,367 A | * 4/1995 | Schulmann et al. .......... 607/61 |
| 5,697,384 A | * 12/1997 | Miyawaki et al. .......... 128/899 |
| 5,792,208 A | * 8/1998 | Gray ........................... 607/36 |
| 5,833,603 A | * 11/1998 | Kovacs et al. ............... 600/317 |
| 5,955,776 A | 9/1999 | Ishikawa ..................... 257/618 |
| 6,034,296 A | * 3/2000 | Elvin et al. ................... 623/16 |
| 6,038,480 A | * 3/2000 | Hrdlicka et al. ............ 607/116 |

* cited by examiner

*Primary Examiner*—Kevin Shaver
*Assistant Examiner*—Navin Natnithithadha
(74) *Attorney, Agent, or Firm*—Howison, Thoma & Arnott, L.L.P.

(57) ABSTRACT

A substantially spherical semiconductor ball implanted in orthopedic structures for sensing and/or stimulation. In one embodiment, a vertebral column (800) having a number of intervertebral discs (802) interspersed among respective vertebral bodies (804), material placed in intervertebral discs (802) allows for a semi-synthetic vertebral disc (806) to be constructed. The artificial intervertebral disk (806) contains one or more ball sensors (808) located within the body of the disk (806) in order to monitor the compression forces. Conventionally, the semi-synthetic disc (806) is monitored only retrospectively, and visualized on x-ray. In this particular embodiment, any of a number of semi-synthetic intervertebral discs (806) can be implanted with one or more ball sensors (808) such that stress and compression forces can be monitored to assure proper alignment of vertebrae (810) in the vertebral column (800), and to monitor the development of any nonphysiologic forces due to vertebral degeneration, disk malfunction, and so on.

16 Claims, 14 Drawing Sheets

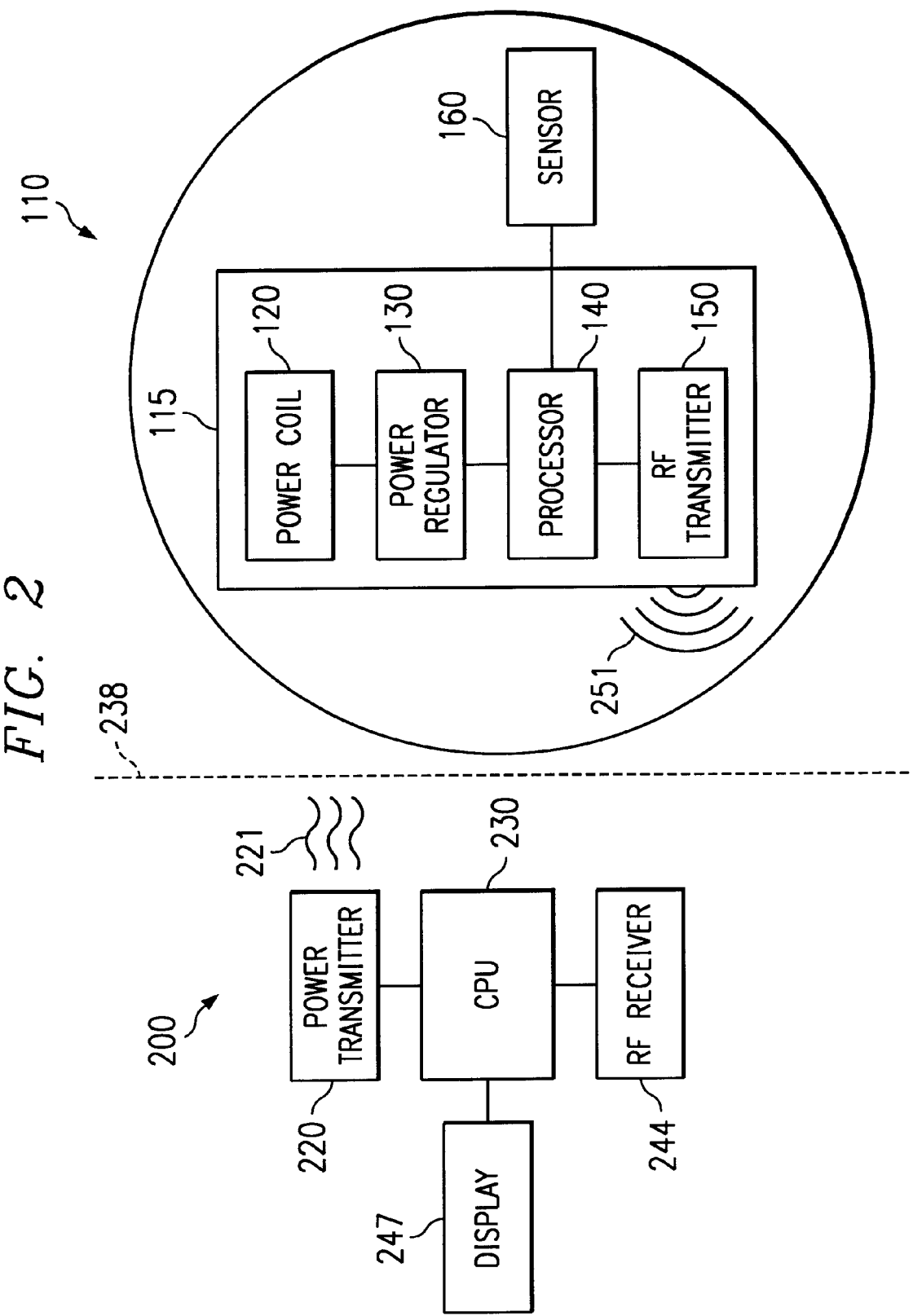

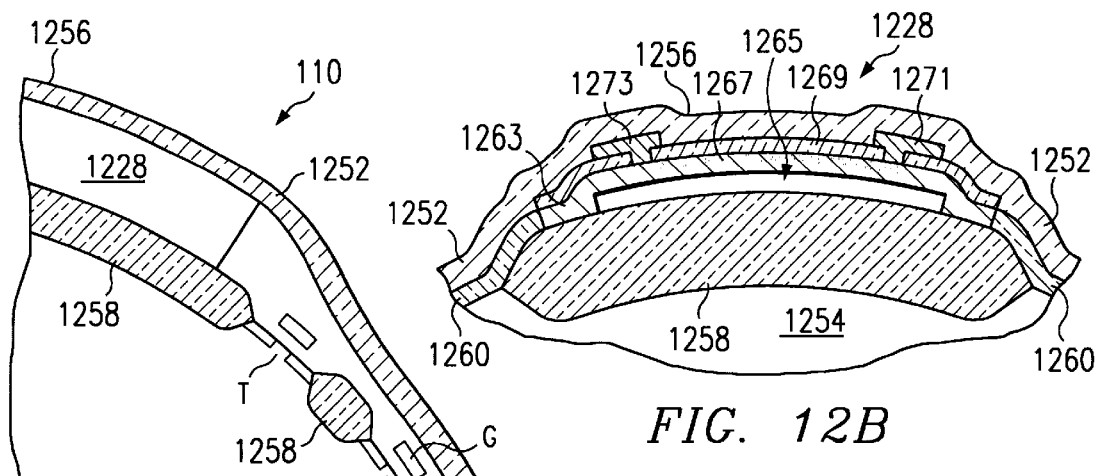
FIG. 12B
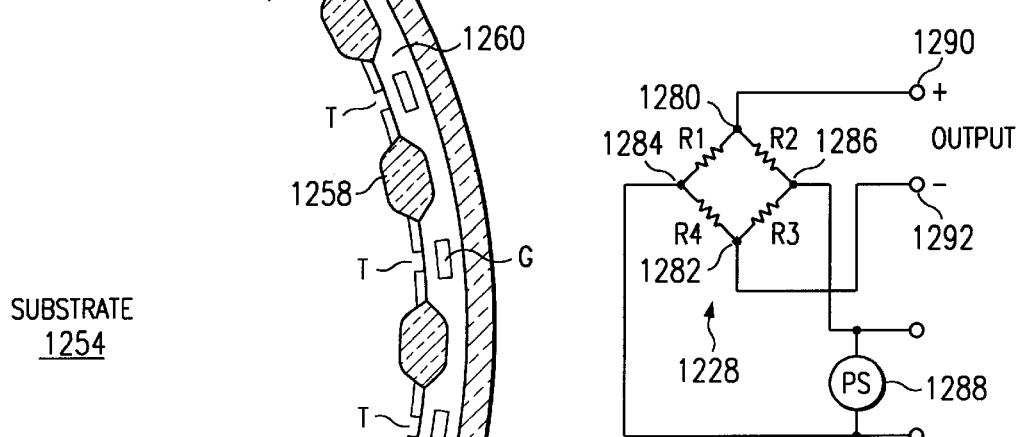
FIG. 12C
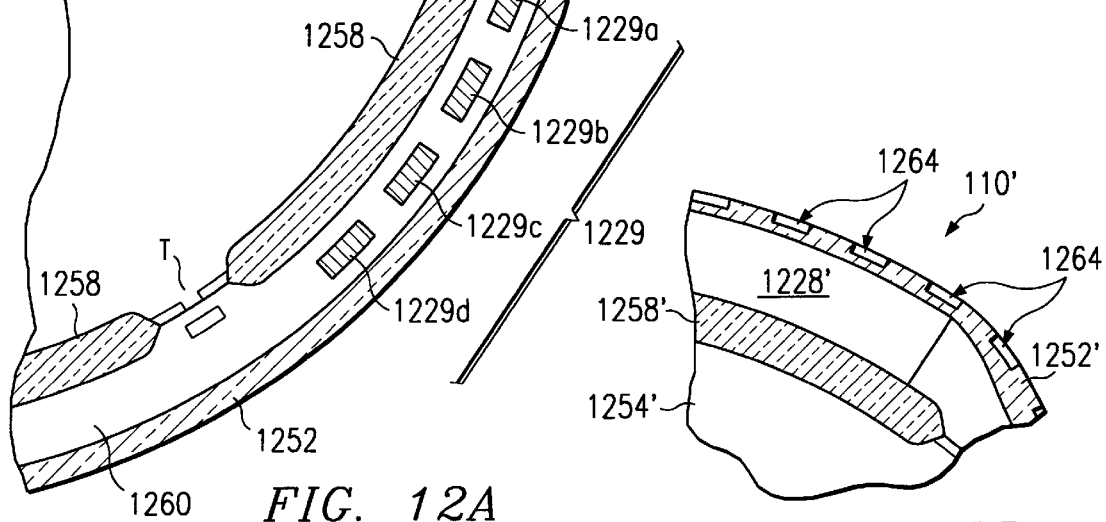
FIG. 12A
FIG. 12D

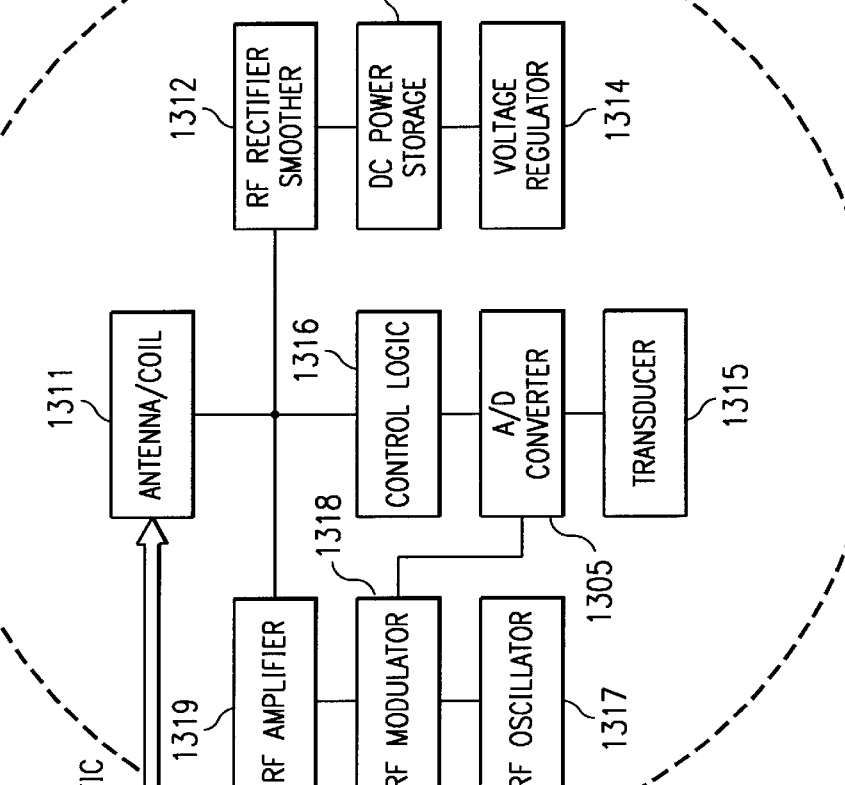
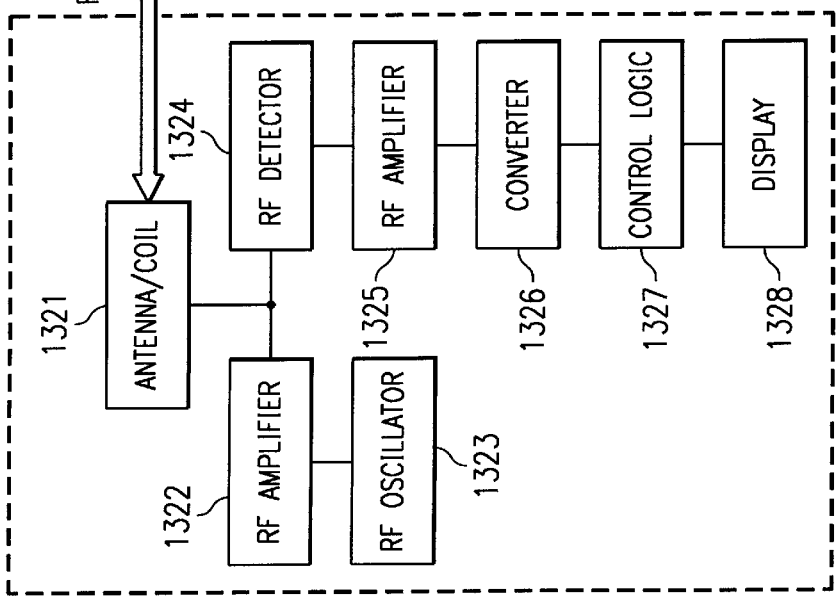
FIG. 13

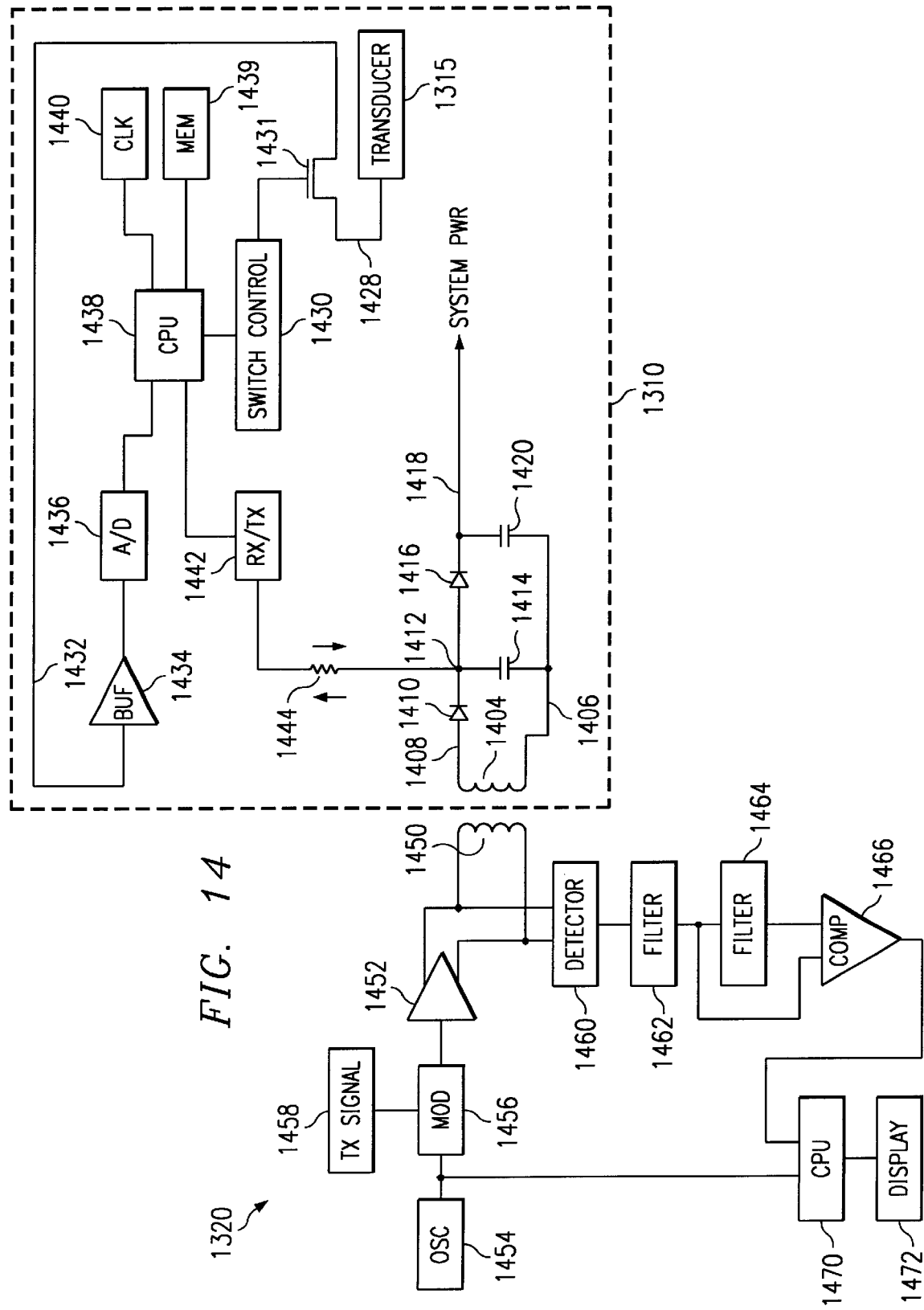

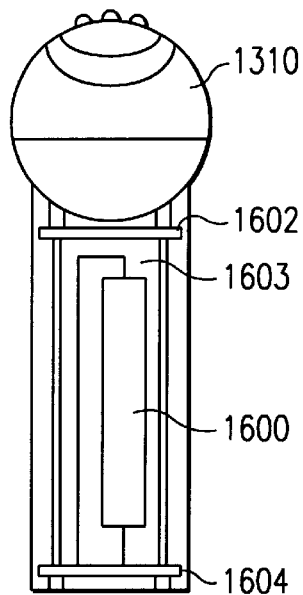
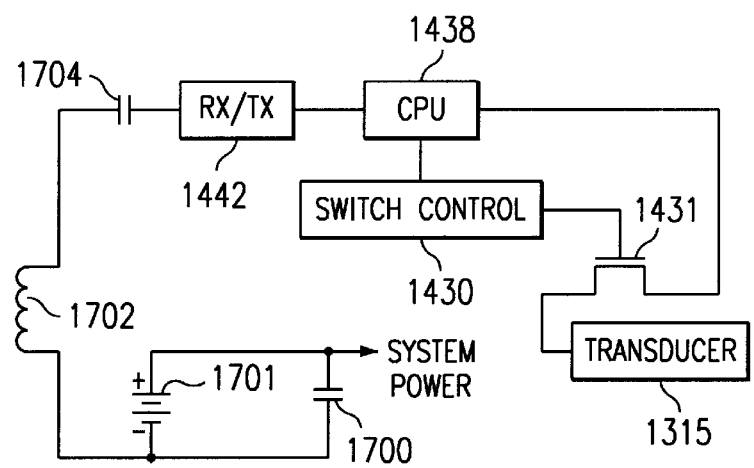
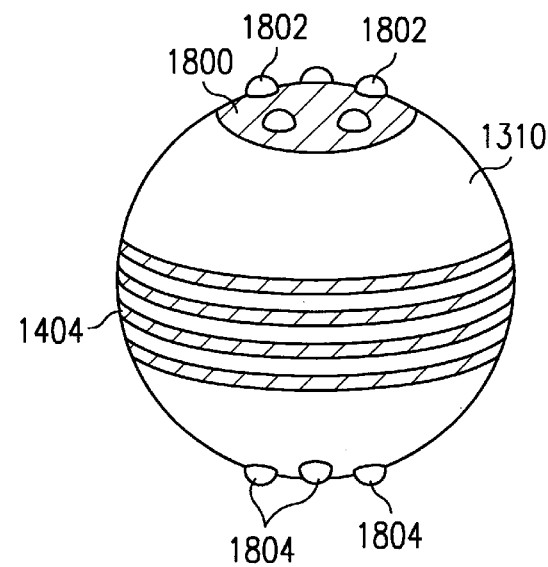
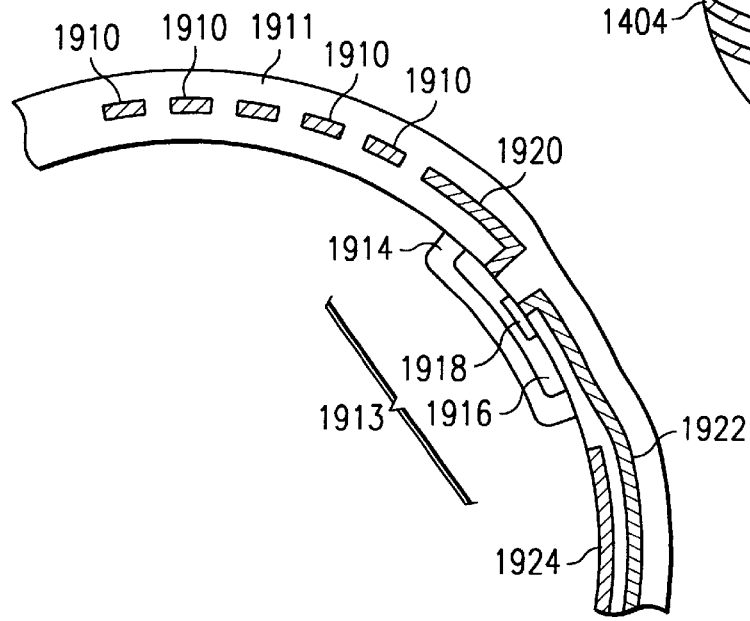

MINIATURE IMPLANTED ORTHOPEDIC SENSORS

CROSS-REFERENCE TO RELATED APPLICATIONS

This application claims priority under 35 U.S.C. 119(e) from U.S. Provisional Patent Application Serial No. 60/114,400 filed on Dec. 31, 1998, having the same title as this application.

TECHNICAL FIELD OF THE INVENTION

This invention is related to a biomedical device, and more particularly to a spherical-shaped biomedical integrated circuit for diagnostics; electronic patient monitoring; prosthetics; computerized data processing and tracking of device performance; and other invasive biomedical applications involving orthopedic implant prostheses (artificial joints, tendons, bones and bone segments), and internal and external orthopedic fixation devices.

This application is related to the following commonly assigned co-pending U.S. Patent applications: Ser. No. 09/448,642 entitled "Miniature Spherical-Shaped Semiconductor With Transducer;" Ser. No. 09/448,641 entitled "Intraluminal Monitoring System;" Ser. No. 09/448,781 entitled "Spherical-Shaped Biomedical IC;" Ser. No. 09/448,678 entitled "Method of and System for Identifying Medical Products;" Ser. No. 09/448,638 entitled "Internal Thermometer;" and Ser. No. 09/448,644 entitled "Monitor for Interventional Procedures;" each of which were filed on Nov. 24, 1999, and co-pending U.S. patent application Ser. No. 09/475,819 entitled "Injectable Thermal Balls For Tumor Ablation," filed of even date with this application, and each of which is incorporated herein by reference.

BACKGROUND OF THE INVENTION

Invasive and non-invasive orthopedic medical devices are known in the art, some examples of which are described in the BIOMEDICAL ENGINEERING HANDBOOK, Bronzino, CRC Press (1995). Instrumented orthopedic devices to assess performance in situ are also known in the art. However, these devices are limited in performance assessment by the absence of reliable applied sensors to gauge orthopedic device function in situ. In those cases where sensors have been applied to the device, the flat planar surface technology that is conventionally used in the fabrication of these semiconductor integrated circuits further limits the operability and versatility of the devices.

SUMMARY OF THE INVENTION

The invention disclosed and claimed herein comprises, in one aspect thereof, an implantable integrated circuit for use with implantation in an organic medium associated with an organic organism. The integrated circuit includes a substantially spherical shaped substrate. At least one transducer is disposed on the substrate for interacting with the organic medium in which the implantable IC is implanted. The transducer operates in accordance with associated operating parameters. Communications circuitry is associated with the substrate for allowing external interface to the at least one transducer for receiving information therefrom.

In another aspect of the invention, the substantially spherical integrated circuit is implanted in internal and external orthopedic fixation devices.

In a further aspect of the invention, the substantially spherical integrated circuit is implanted in orthopedic prostheses which include artificial joints, and artificial intervertebral disks.

In still another aspect of the invention, the substantially spherical integrated circuit is implanted in an orthopedic medium such as tendons, ligaments, and bone. Transponders which function as position sensors can be temporarily affixed to bone intraoperatively to allow correct positioning of artificial limbs or joints (angle of inclination). Current methodology for alignment of hip joints requires manual and visual means leading to malalignment, a major cause of morbidity in patients undergoing this procedure. Implantable prosthetic devices containing multiple position sensor balls can detect the angle of movement of a prosthetic device. Following artificial knee and shoulder replacement, increasing ranges of movement are required to rehabilitate the joints. Position sensor balls can be programmed to elicit a signal once the goal range of motion is achieved Every few days the goal can be increased to facilitate the recovery period postoperatively. Alternatively, following artificial hip replacement, the range of motion of the hip joint should initially be limited to enhance the long term stability of the prosthetic device. In this instance, a warning signal will be elicited if the angle of motion is exceeded. Each week the limiting range of motion of the hip is increased, again to facilitate the recovery period postoperatively. In further embodiments, transponders determining strain and tensile strength can be implanted in ligaments. For example, transponders implanted in the anterior cruciate ligament can determine the tensile strength of the ligament allowing the physician when to safely instruct the patient to return to progressive activities requiring increasing demands upon the ligament. Current methodology does not apply internal devices to determine proper alignment intraoperatively and monitoring of rehabilitation postoperatively.

In another application, the ball can function as an actuator used to stimulate excitable tissue. The semiconductor ball can function as a TENS (Transcutaneous Electrical Nerve Stimulator) unit to treat chronic pain syndromes. The unit can also be used to stimulate both nerve and muscles in paralyzed or injured limbs to help prevent the development of atrophy or as a means to reduce the inflammatory response. Multiple balls which function as both receivers of electrical signal and also as transmitters of signal may be useful in robotic applications. These sensors and actuators could function as a bridge between an amputated limb and a moveable prosthetic "hand" or provide for an entirely functional robotic prosthetic limb

BRIEF DESCRIPTION OF THE DRAWINGS

For a more complete understanding of the present invention and the advantages thereof, reference is now made to the following description taken in conjunction with the accompanying Drawings in which:

FIG. 2 illustrates a block diagram of a ball IC and an external monitoring and control station, according to a disclosed embodiment;

FIG. 12A illustrates additional semiconductor details of the ball IC in cross section;

FIG. 12B, there is illustrated an implementation of the transducer in cross section;

FIG. 12C, there is illustrated a conventional strain gauge circuit according to the device structure of FIG. 12B;

FIG. 12D shows a modification of the embodiment of FIG. 12A;

FIG. 13 illustrates a more detailed block diagram of an alternative embodiment having basic circuit functions of an external control system and a ball IC;

FIG. 14 illustrates a schematic block diagram of the control system and the ball IC for the powering/detection operation;

FIG. 16 illustrates a side view of an alternative embodiment utilizing additional circuitry or structure attached to the ball IC for providing a local power source;

FIG. 17 illustrates a schematic block diagram of the ball IC using a battery as the local power supply system;

FIG. 18 illustrates a perspective view of the ball IC, wherein an inductive element is illustrated as being strips of conductive material wrapped around the exterior of the ball IC;

FIG. 19 illustrates a cross-sectional diagram of the surface of the ball IC illustrating the conductive strips forming the inductive element;

DETAILED DESCRIPTION OF THE INVENTION

The Ball Semiconductor IC

The orthopedic spherical semiconductor sensor ball disclosed herein offers a number of advantages over conventional semiconductor devices having a planar or two-dimensional geometry. For example, many biomedical applications which include measurement and instrument functions can be performed by the disclosed ball sensor. By way of illustration, a few of these advantages include the following: a spherical device has a smooth, rounded shape which is easily implanted or injected into a biological medium and which passes easily through a biological medium, if necessary in a particular application. Further, the large surface area of a spherical device relative to its overall dimensions provides for the maximum of surface area devoted to functional regions in contact with the biological medium, such as transducers and other circuitry. Further, the spherical device permits the disposition of onboard semiconductor devices to be aligned on all three geometric axes for maximum function on a single substrate. A spherical-shaped integrated circuit (IC) has been disclosed by Applicant in U.S. Pat. No. 5,955,776 entitled "Spherical Shaped Semi-conductor Integrated Circuit," which issued Sep. 21, 1999, and which is herein incorporated by reference. Such a spherical-shaped IC, which may also be ovoid-shaped or ellipsoid-shaped, is also sometimes referred to herein simply as a ball, a ball semiconductor, a semiconductor ball or a ball semiconductor IC.

The versatility of the spherical-shaped IC further extends to all types of transducers, including use in both sensing applications as well as actuating applications and even combinations thereof. It is well known, for example, that a transducer inherently, in many cases, has the capability to either sense a condition or to actuate a condition or both, depending on how it is configured or used in a particular application. Numerous embodiments having both transduction capabilities will be described in the present disclosure. However, the examples described are intended to be illustrative, and not limiting of the many and varied possible embodiments and alternative uses to which the inventions of the present disclosure may be applied.

Figure 1:
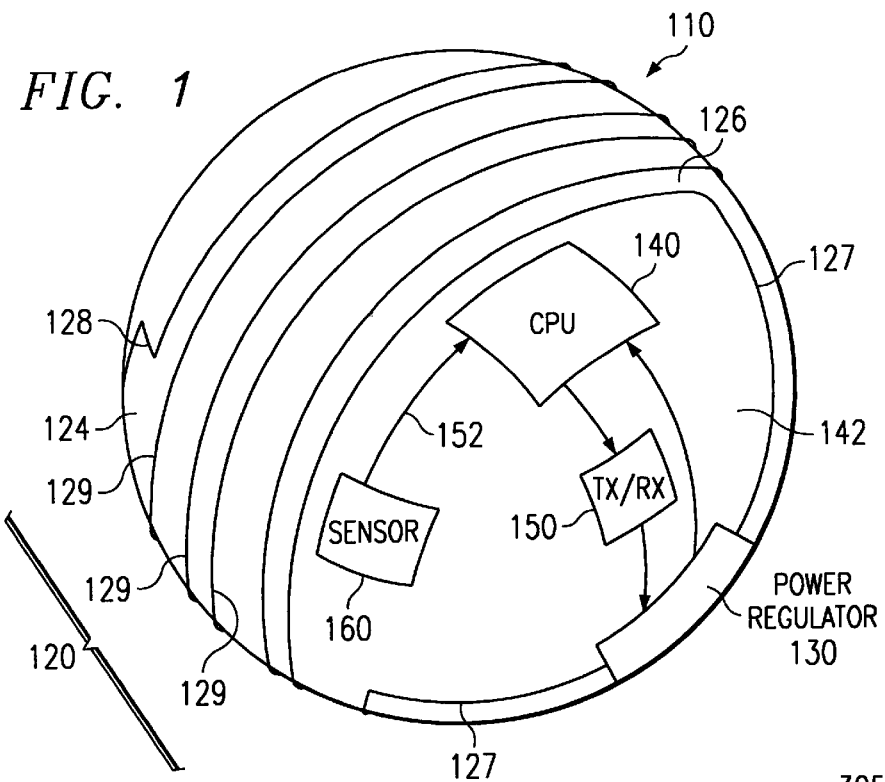
FIG. 1 illustrates one embodiment of a ball IC having power and sensing capabilities.

Referring now to FIG. 1, there is illustrated one embodiment of a ball IC 110 having power and sensing capabilities. A power source for the semiconductor ball 110 is the inductance coil 120 which becomes energized by a separate nearby source (not shown) which provides a varying magnetic field for inducing electric energy into the inductance coil 120. The inductance coil 120 is formed of a conductive path or wire 128 which is wound on the surface of a substrate 142 around the semiconductor ball 110, with non-conductive spaces 124 and 126 between windings 129. The inductance coil 120 is coupled with a power regulator 130 via a conductive path 127 which provides a relatively constant DC voltage of about 3 volts to the circuits on the ball 110, with power stored in an internal capacitor (not shown). (Note that as advances in technology permit, the required voltage levels to power the onboard circuits may be less then the disclosed 3 volts.) An onboard processor 140 connects to the power regulator 130 to obtain power therefrom, and it can be appreciated that the processor 140 could be configured to also route power through from the power regulator 130 to other onboard circuits, such as a radio frequency (RF) communication circuit 150 and one or more transducers 160. In any case, the processor 140 connects to both the RF communication circuit 150 and the transducer 160 for monitor and control thereof. The transducer(s) 160 are fabricated on or near the surface of the ball 110 where exposure to a portion of a biological medium in which a parameter is to be sensed or affected by an actuator is better accommodated. The transducer 160 is coupled to the processor 140 via a line 152.

Alternatively, the ball IC 110 may be powered by a miniature battery (not shown, but illustrated and discussed in greater detail hereinbelow) which is connected to the ball 110, as well as to clusters of similar balls with different functions, such as a memory. The miniature battery may also have a substantially spherical shape to accommodate a common connection scheme between adjacent balls. Preferably, such battery balls may be an electric double layer condenser formed of such materials as manganese dioxide, lithium, carbon or lithium ion, etc. Since such a battery ball provides a greater capacity energy source than radio frequency energy generated through the inductance coil 120, longer communication distances can be achieved.

The inductance coil 120 has ends (not shown) that are connected by subsurface conductors (not shown) to the other circuit elements on the ball 110. It will be appreciated that the inductance coil 120 may have many more windings 129 than the 5–6 windings actually shown. The signal processor 160 provides an output to a transmitter 150 that preferably radiates an RF signal to a receiver (not shown) at another location. Both the magnetic field generator and receiver can be included in a common computer-controlled apparatus or central processing unit (CPU) station within proximity of the ball 110, at least when its operation is required.

Referring now to FIG. 2, there is illustrated a block diagram of a ball IC and an external monitoring and control station, according to a disclosed embodiment. A dashed line 238 separates the ball IC 110 on the right side, as deployed within the patient's body, from an external control station 200, on the left side of the illustration, and located outside of the patient's body. The station 200 includes a CPU 230 that is in communication with and controls a power transmitter 220, an RF receiver 244, and a display panel 247. When the station 200 is in proximity to the patient's body so that it can communicate with the ball IC 110, the CPU 230 initiates an query to the ball 110 by powering up the power transmitter 220. The power transmitter 220 directs low frequency electromagnetic radiation 221 at the patient's body and ball 110 therein. The varying magnetic field component of the electromagnetic radiation 221 induces a current in the power coil 120 of the ball 110. The power regulator 130 then converts the AC current induced in the power coil 120 to DC current, which is then regulated by the regulator 130 to provide a relatively constant voltage level (e.g., three volts) to the other circuits of the ball 110, including the processor 140, transducer 160, and RF transmitter 150. Note that an alternative to using separate coils for the inductance or power coil 120 and RF transmitter 150, a single antenna coil could be used. This dual-purpose alternative coil is described by Applicant in a commonly-assigned U.S. Pat. No. 5,955,776, issued Sep. 21, 1999 and entitled "Miniature Spherical-Shaped Semiconductor With Transducer," referenced hereinabove.

Once energized in the aforementioned manner, the ball 110 can sense a quantitative condition as measured by the sensor 160 (or provide electrical stimulation, as one example of an actuator function). Specifically, in this disclosed embodiment, the ball 110 can be implanted in bone, ligaments, and cartilage to sense pressure, tensile strength, strain, position, and compression conditions associated with prosthetics and surgically implanted devices. These transponders allow the physician to properly implant the devices, and allow the physician to monitor and assess rehabilitation of the tissue postoperatively. The processor 140 (for example, a digital signal processor which also comprising analog-to-digital conversion capabilities) then preferably converts the electrical signals from the transducer 160 into digital data for accurate transmission out to the station 200. The digital data signals representing the measured parameter are then modulated onto a carrier frequency signal by the RF transmitter 150 and transmitted by radio waves 251 outside of the body for reception by the RF receiver 244. The CPU 230 then demodulates the RF carrier frequency signal to extract the measured parameter data, and stores the data in a computer memory (not shown, but discussed in detail hereinbelow). The CPU 230 can also report the measured data to the patient or a technician by means of the display 247.

Systems that energize and interrogate remote electronic devices using electromagnetic energy and RF communication are well known. Such remote electronic devices are sometimes referred to as passive transponders. Examples are described in the following U.S. Pat. No. 4,345,253, entitled "Passive Sensing and Encoding Transponder," issued Aug. 17, 1982; U.S. Pat. No. 4,857,893, entitled "Single Chip Transponder Device," issued Aug. 15, 1989; U.S. Pat. No. 5,252,962, entitled "System Monitoring Programmable Implantable Transponder," issued Oct. 12, 1993; and U.S. Pat. No. 5,347,263, entitled "Electronic Identifier Apparatus and Method Utilizing a Single Chip Microcontroller and an Antenna Coil," issued Sep. 13, 1994, which are hereby incorporated by reference.

Physiological Monitoring Using Sensors on the Ball IC

Some examples of physiological conditions, parameters, and variables which can be measured are obtained through the insertion of one or more ball ICs into a bone, tendon or ligament for measuring the desired quantitative conditions, for example, assessing stress, position, tensile strength, or compression forces. Similarly, the disclosed architecture is beneficial in monitoring the stress or compression forces generated on vertebral discs in individuals required to lift heavy objects, as well as post-menopausal women who frequently develop vertebral compression fractures secondary to osteoporosis. Movement of prosthetic limbs is currently not well coordinated because of the size required of instruments used to control artificial limb function. Small spherical-shaped semiconductors will allow this instrumentation to be decreased in size and allow for connection between nerve endings and robotic instrument controlling functional hand and finger movements. Similar features could also be envisioned to control lower extremity prosthetic limbs.

Figure 3:
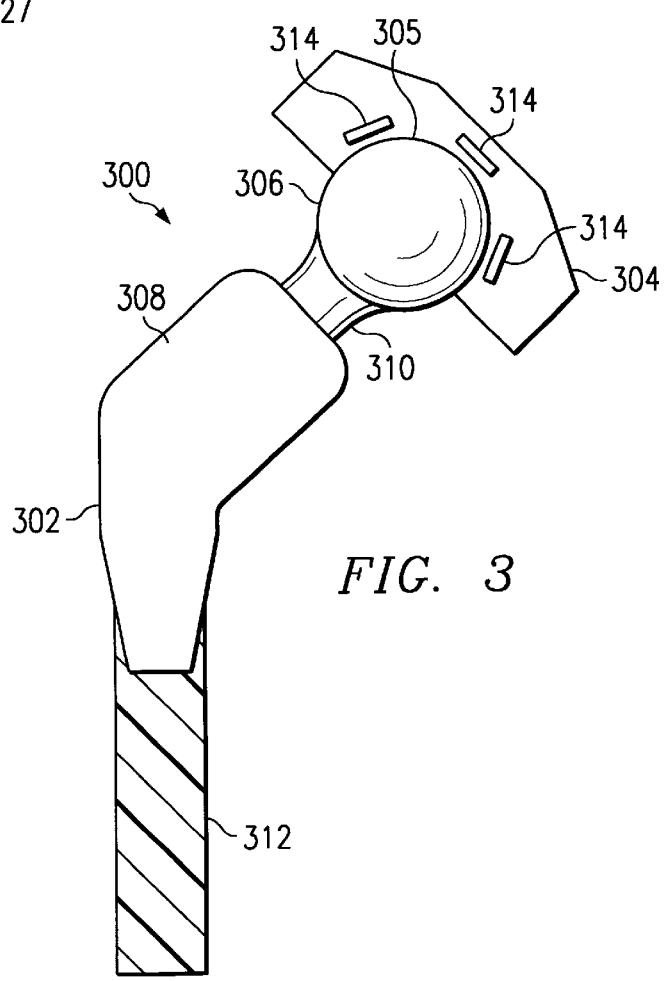
FIG. 3 illustrates an alternative embodiment having an instrumented prosthetic of a composite orthopedic hip prosthesis with ball-containing force sensors attached to the acetabular cup, adjacent to the femoral head/acetabular interface.

Referring now to FIG. 3, there is illustrated an alternative embodiment having an instrumented prosthetic of a composite orthopedic hip prosthesis with ball-containing force sensors attached to the acetabular cup, adjacent to the femoral head/acetabular interface. The prosthetic 300 has a joint member 302 which rotatably couples to socket member 304. The joint member 302 meets the socket member 304 via a ball member 306 which inserts into the socket member 304 to form an interface 305. The ball member 306 is fixed to one end of a main body portion 308 of the joint member 302 via a neck section 310. The other end of the main body portion 308 is fixed to a shaft 312. To monitor the integrity of the coupling of the ball member 306 to the socket member 304, one or more ball sensor strain gauges 314 are affixed or implanted into the socket member 304 in proximity to the interface 305. One additional parameter which could be of interest is the temperature generated by the action of the mechanical joint, which could be indicative of the amount of free motion exhibited by the joint. Another parameter, which could be monitored in conjunction with the temperature, is the pressure exerted at the joint interface 305 to attain the measured temperature. Both of these measured parameters can be informative as to the integrity or quality of the mechanical joint of the prosthetic. Similarly, in circumstances where the prosthetic 300 is used in conjunction with the socket member 304 being normal bone, strain, temperature and pressure measurements can be made in the normal bone which could provide the socket portion 304 by implanting the ball sensors on or into the normal bone structure at the site of the interface 305.

Figure 4A:
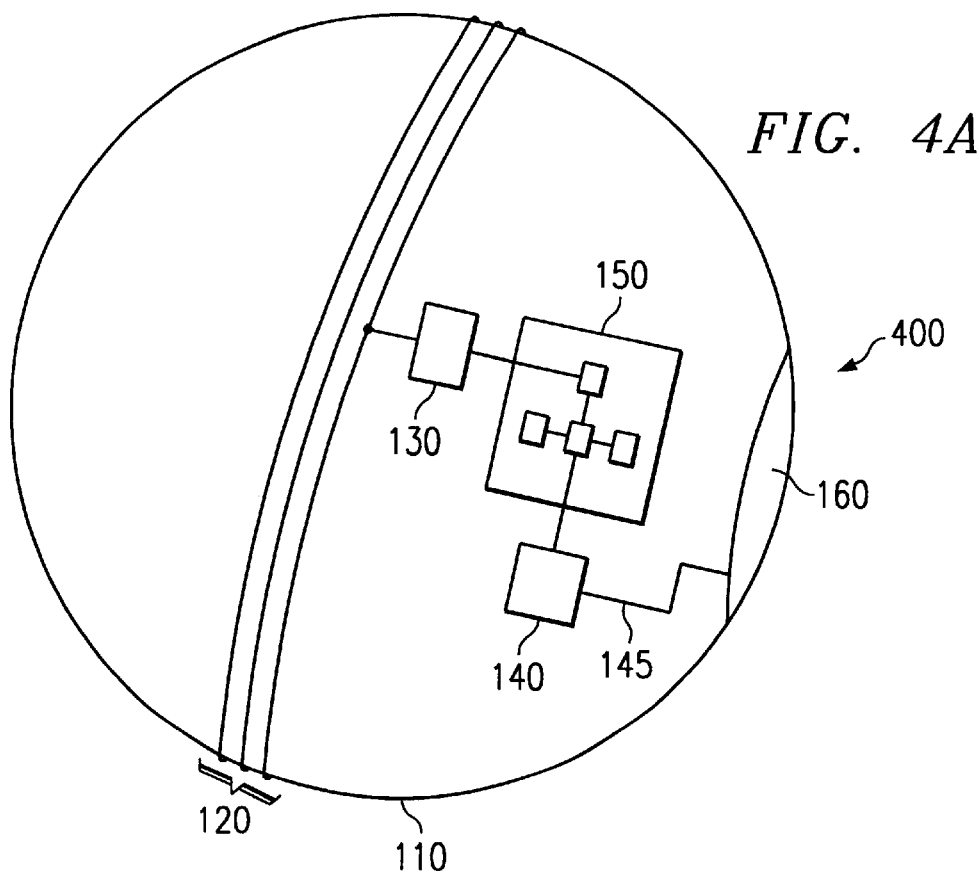
FIG. 4A illustrates an alternative embodiment having a ball IC with strain gauge sensor (as illustrated in more detail in FIG. 12C)

Referring now. to FIG. 4A, there is illustrated an alternative embodiment having a ball IC with strain gauge sensor (as illustrated in more detail in FIG. 12C). The sensor 160 is shown as fabricated on a portion of the surface of the ball IC 110, the portion contacting the medium to be measured. The sensor 160 connects over a line 145 to the processor 140 which digitizes the sensor data. Digitized data from processor 140 is applied to the RF transmitter 150 for modulation of the digitized data on an RF signal using, for example, Frequency-Shift Keying (FSK) techniques. The RF transmitter 150 connects to the power regulator circuit 130 for receiving power therefrom, and for transmitting signals therethrough to the antenna coil 120.

Figure 4B:
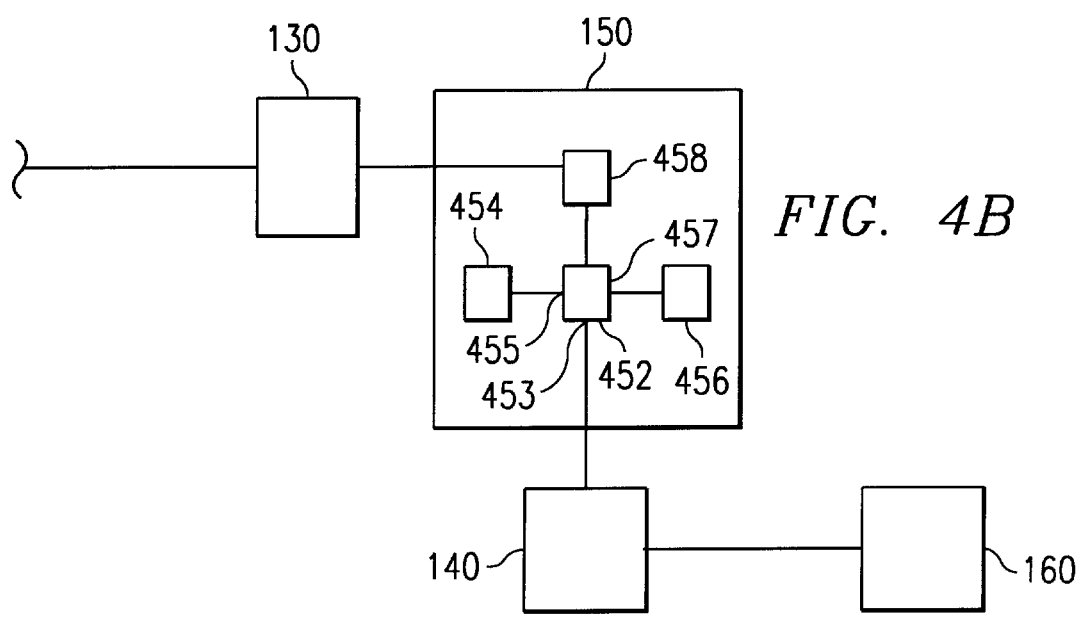
FIG. 4B illustrates a more detailed block diagram of the RF transmitter/receiver circuit of the ball IC.

Referring now to FIG. 4B, there is illustrated a more detailed block diagram of the RF transmitter/receiver circuit of the ball IC. As shown in FIG. 4B, the RF transmitter 150 comprises a mixing circuit 452, first and second RF oscillators 454, 456, and an amplifier 458. In particular, the signal from the sensor 160 corresponding to the level of strain and digitized by processor 140 is applied to one input 453 of mixing circuit 452. A first high frequency signal from RF oscillator 454 is applied to a second input 455 of mixing circuit 452, and a second low frequency signal from RF oscillator 456 is applied to a third input 457 of mixing circuit 452. The mixing circuit 452 modulates the incoming packet of digital information between a high frequency signal from RF oscillator 454 for use in generating each logic "high" bit of data in the information packet; and a low frequency signal from RF oscillator 456 for use in transmitting each logic "low" bit of data in the information packet. The resulting FSK signal is amplified by amplifier 458 and applied to the coil 120 for transmission to RF receiver 244 (shown in FIG. 2) of the remotely located control station 200.

The disclosed strain gauge sensor is conventional is well known in the art. See, for example, ELECTRONIC ENGINEER'S HANDBOOK, 2nd Edition, Fink Christianson, McGraw Hill (1982), and BIOMEDICAL ENGINEERING HANDBOOK, Joseph D. Bronzino, Editor-in-Chief, CRC Press (1995). Fabrication of these kind of sensors can be readily adapted to a ball IC using the fabrication techniques described in U.S. Pat. application No. 5,955,776, issued Sep. 21, 1999, referenced above. The performance of the sensor ball IC 110 can be protected from body tissues, or other of the body's defensive mechanisms by encapsulation of the device within a polymeric or gel coating albumin, or a "bio-coating." Examples of such encapsulation are described in the following U.S. Pat. No. 4,530,974 by Munro et al., entitled "Nonthrombogenic Articles Having Enhanced Albumin Affinity," issued Jul. 23, 1985; and U.S. Pat. No. 5,017,670 by Frautchi et al., entitled "Methods And Compositions For Providing Articles Having Improved Biocompatibility Characteristics," issued May 21, 1991, both of which are incorporated herein by reference. The sensor 160 shown in FIG. 4A is readily adaptable by suitable reconfiguration to sense other physiological parameters such as pH, chemical parameters, and variables as described previously, and physical parameters such as pressure, movement, temperature and the like. Thus, the example described in FIGS. 4A and 4B is intended to be illustrative and to not limit the disclosed embodiment.

In applications where information regarding ionic activity or concentration is sought, one embodiment of a sensor 160 utilizes an ion-sensitive field effect transistor ISFET which is essentially an insulated gate field effect transistor (IGFET) without its metal gate. The operation of the ISFET is similar to that of IGFET if one considers the reference electrode and the electrolyte into which the semiconductor ball is placed as the modified gate. In operation, the interfacial potential of the electrolyte-insulator interface produced by the net surface charge due to the ionization and complexation with the ions in a solution will affect the channel conductance of the ISFET in the same way as the external gate voltage applied to the reference electrode. The drain current of the ISFET is therefore a function of the electrolytes in solution for a constant drain-source voltage. Various materials can be used for the gate insulators, such as $SiO_2$, $Si_3N_4$ and $Al_2O_3$. For pH sensors, $Si_3N_4$ and $Al_2O_3$ provide satisfactory performance.

ISFET's for other ions such as $K^+$, $Na^+$, and $Ca_2^+$ may have a layer coated over the gate insulator of valinomysin in PVC, aluminosilicate, and dedecyl phosphonate, respectively.

Figure 5:
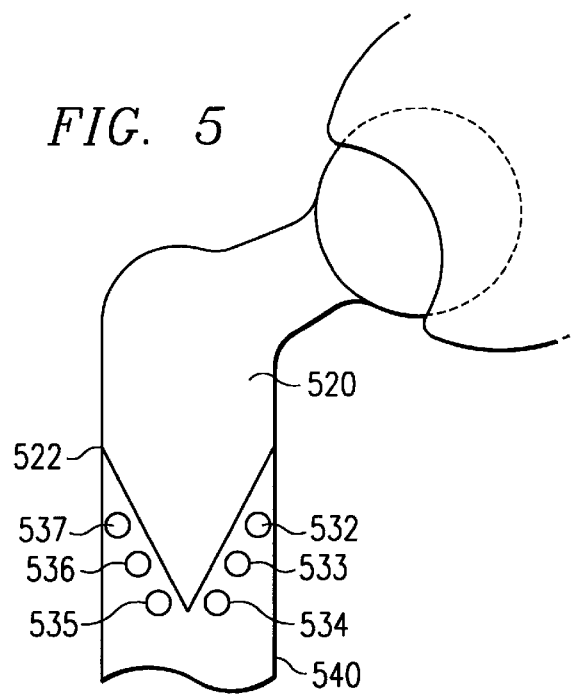
FIG. 5 illustrates an array of sensor balls used in conjunction with an artificial hip joint implant.

Referring now to FIG. 5, there is illustrated an array of sensor balls used in conjunction with an artificial hip joint implant. Sensor balls 532–537 are implanted in normal bone 540 along an artificial/tissue interface 522 of an artificial hip joint 520 to assess tensile (or compressive) forces, and any other parameters such as acceleration, movement, to monitor for instability and proper hip joint function. This embodiment provides, for example, early warning of the need for revision arthroplasty.

Figure 6:
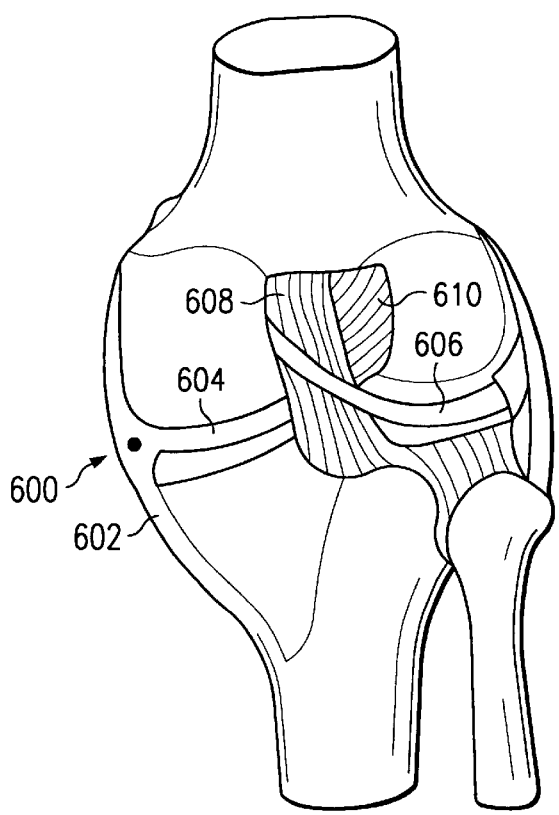
FIG. 6 illustrates a sensor implant in a cartilage or ligament region of a right knee within the intra-articular space of the knee joint to monitor intra-articular pressure.

Referring now to FIG. 6, there is illustrated a sensor implant in a cartilage or ligament region of a right knee within the intra-articular space of the knee joint to monitor intra-articular pressure. A sensor 600 is illustrated as being implanted along the tibial collateral ligament 602, which is a portion of the joint capsule of the knee. Pressure measurements can be made to assess any degradation in the operable strength of the ligament during a patient's recovery, or even during everyday activity. Similarly, the sensor 600 may be implanted within the cartilage surface of any meniscus of the knee (medial 604 or lateral 606) to assess the integrity of the cartilage at these points in the knee. Note that the ball sensor is of such size and versatility to be implantable in many other areas of the knee, for example, the posterior cruciate ligament 608, anterior cruciate ligament 610, etc. As is true of most implantable sensors 600, they will be coated with biocompatible materials such as iridium oxide on top of a thin titanium layer as is used to coat conventional invasive mechanisms, for example, a long-term indwelling accelerometer sensor used in implantable pacemakers.

Figure 7:
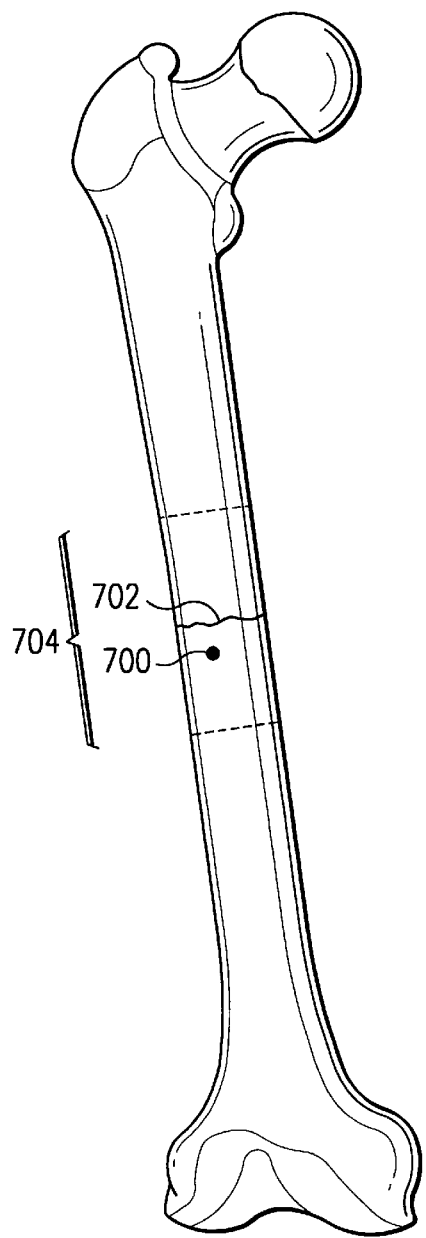
FIG. 7 illustrates a position/stress transducer placed in normal bone to detect stress at a site near the placement of an external fixation device to measure the extent of bone extension, stress remodeling and healing in an Ilizarov procedure.

Referring now to FIG. 7, there is illustrated an embodiment of a ball sensor used as a stress monitor at a bone fracture site and placed in normal bone to detect stress and tensile strength at a site near the placement of an external fixation device to measure the extent of bone extension, stress remodeling, and healing in an Ilizarov procedure. The ball sensor 700 is versatile for use in stimulation, therapy, and treatment of bone fractures 702 along an Ilizarov fracture site 704. The optimal time to adjust the compressive or tensile forces applied to bone fracture interfaces 702 to maximize the rate of healing in Ilizarov external fixation compression or tension-generating procedures is largely determined by qualitative, rather than quantitative criteria. (The Ilizarov system utilizes hinge and translation mechanisms which are specifically oriented for a given case. Complex deformities are addressed by frames that include hinge (rotation) and translation mechanisms in series or stages.) Placement of stress- and/or position-measuring sensor ball (or ball arrays) in the vicinity of the fixator can provide objective data upon which to adjust the desired tension or compression level.

Prosthetics and Artificial Organs

Prosthetics devices are commonly used to replace a missing body part such as a limb. Likewise artificial bones and vertebral disks are often used to replace or function as other orthopedic structures. Providing smart technology to prosthetics and artificial organs allow greater versatility in operation and/or monitoring of these parts and the body regions in which they are placed. Currently, proper alignment of the angle of inclination of the prosthetic hip joint is determined by manual and visual means. This can lead to improper alignment of the joint, chronic pain, limited mobility, and the potential for one extremity to be shorter than the other. Placement of semiconductor position transponders upon the prosthetic device, femoral shaft, and acetabular cup allows for proper angle of inclination placement and equal lower extremity length.

Figure 8:
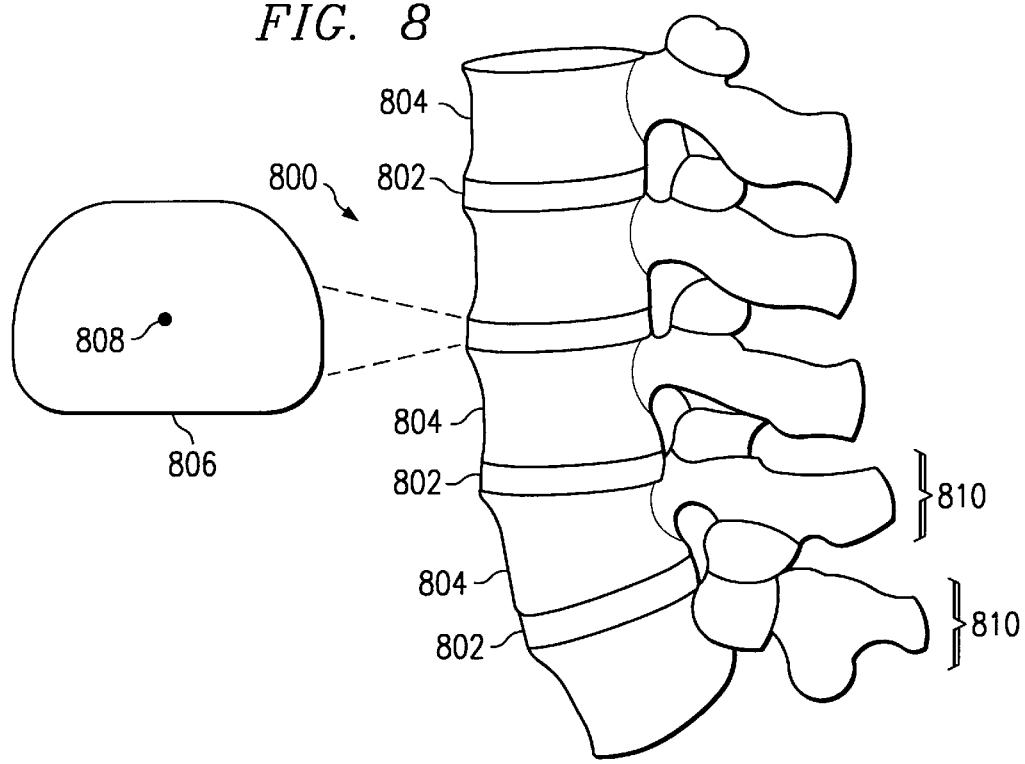
FIG. 8 illustrates an embodiment of a vertebral column having an artificial intervertebral disk with an array of ball sensors located within the body of the disk in order to monitor the compression forces in the disk.

Referring now to FIG. 8, there is illustrated an embodiment of a vertebral column having an artificial intervertebral disk with an array of ball sensors located within the body of the disk in order to monitor the compression forces in the disk. In a vertebral column 800 having a number of intervertebral discs 802 interspersed among respective vertebral bodies 804, material placed in intervertebral discs 802 allows for a semi-synthetic vertebral disc 806 to be constructed. Conventionally, the semi-synthetic disc 806 is monitored only retrospectively, and visualized on x-ray. In this particular embodiment, the semi-synthetic intervertebral disc 806 can be implanted with one or more ball sensors 808 (similar to ball sensor 110) such that stress and compression forces can be monitored to assure proper alignment of vertebrae 810 in the vertebral column 800, and to monitor the development of any nonphysiologic forces due to vertebral degeneration, disk malfunction, and so on.

Figure 9:
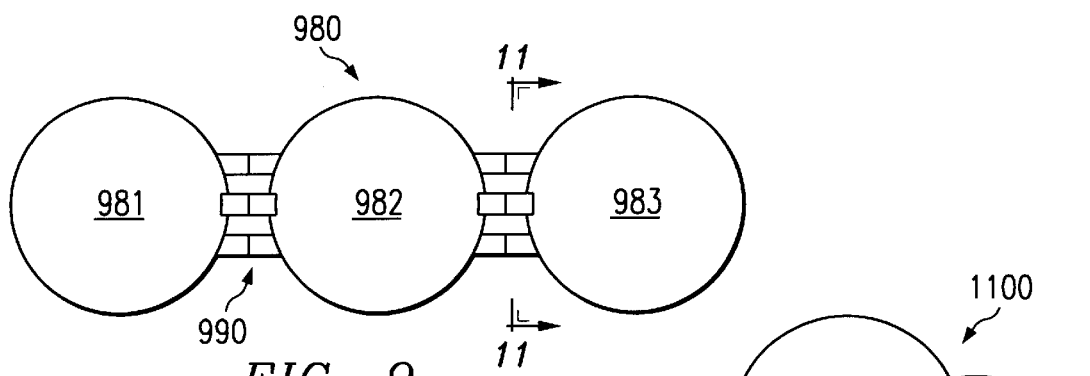
FIG. 9 illustrates a side elevation of a cluster of three semiconductor balls that may be employed in a cooperative function.

Referring now to FIG. 9, there is illustrated a side elevation of a cluster of three semiconductor balls that may be employed in a cooperative function. Although a single ball can include the foregoing functions, more complex monitoring functions with multiple transducers can be implemented using multiple ball systems attached to prosthetics, catheters, needles and other medical-related apparatus. For example, ball 981 (similar to ball sensor 110) can include power receiving and data transmission functions. Alternatively, ball 981 can be a miniature ball-shaped battery. Ball 982 can include a first transducer function, such as pressure sensing, and ball 983 can include a second transducer function, such as measuring strain, pH, $pO_2$, $pCO_2$, or temperature, as the particular application requires. Connections between the balls are made through metal contacts 990, which may be solder bumps, and as described in greater detail hereinbelow, the metal contacts 990 may be used for a variety interface functions, such as power, data, and a signal bypass path.

Figure 10:
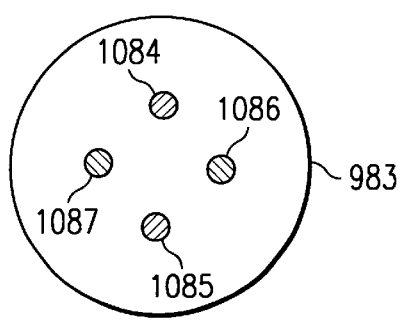
FIG. 10 illustrates a cross section taken through the line 11—11 of FIG. 9.

Referring now to FIG. 10, there is illustrated a cross section taken through the line 11—11 of FIG. 9. As mentioned hereinabove, the contacts 990 may be employed to interface a variety of functions. For example, the contacts 1084 and 1086 may be power contacts, such as a positive 3.0 volts and ground, which can be passed from ball 981 (if ball 981 were to provide the power function for the set 980) to ball 982, and then around ball 982 to ball 983 by conductors on the surface of ball 982 using two of a group of similar contacts of contacts 990 to power ball 983. The contacts 1085 and 1087 may be data and control contacts for communications between balls of the set 980. Similar data and control contacts may exist among contact group 990 between ball 982 and ball 983 to the extent needed.

Figure 11:
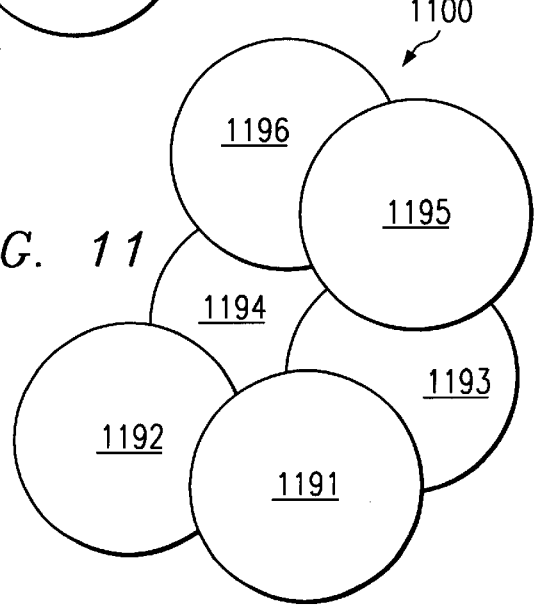
FIG. 11 illustrates a 3-D ball cluster in a cooperative orientation.

Referring now to FIG. 11, there is illustrated a 3-D ball cluster in a cooperative orientation. As an example of the versatility of such ball systems is illustrated where the cluster 1100 specifically shows six balls 1191, 1192, 1193, 1194, 1195 and 1196 (all similar to ball sensor 110), arranged in a three-dimensional configuration. It will be appreciated that various other cluster arrangements are possible which have fewer balls, and are limited only by the constraints of the end-use application. Each of the balls 1191, 1192, 1193, 1194, 1195 and 1196, of the cluster 1100 can perform different electronic functions, and communicate with each other through contacts (not shown here, but discussed in detail in FIGS. 9 and 10). Such cluster arrangements can provide a mix of, for example, three battery balls 1191, 1992,and 1193, which provide ample power for the remaining energy-consuming balls, according to the functions provided. Such a mix may be necessary where a heating application is required for, for example, tumor ablation, or for more precise heating applications related to cartilage or ligament treatment.

Referring now to FIG. 12A, there are illustrated additional semiconductor details of the ball IC. The ball IC 110 is hermetically protected by a thin exterior glass passivation layer 1252, which may be phosphosilicate glass. The interior of the ball IC 110 comprises a semiconductor substrate 1254 (similar to substrate 142), which may be doped p-type or n-type in accordance with the particular requirements of the fabrication process. Optionally, the substrate 1254 may be connected to the metallic intraluminal or a prosthetic device to serve as a ground potential for the ball IC 110. A transducer 1228 has an outer surface 1256 that is exposed to the desired medium. The transducer 1228 preferably is formed atop a thick dielectric layer 1258, which may be a field oxide layer grown on the substrate 1254.

A large number of transistors T make up the circuitry of the voltage regulator 130, processor 140 and RF transmitter 150, described above in connection with FIGS. 1 and 2. Although these transistors T are depicted schematically as field-effect transistors, the integrated circuitry of the ball IC 110 could also use bipolar transistors. The individual transistors T are shown separated by portions of the field oxide 1258. Transistor gates G and circuit interconnections (not shown) are embedded in an inter-level dielectric layer 1260 and are made using conventional semiconductor fabrication techniques adapted to the spherical surface of the ball IC 110.

The power coil 1229 (as described in connection with inductance/power coil 120 of FIGS. 1 and 2), is shown as having a plurality of separate windings 1229a, 1229b, 1229c and 1229d, which may be fabricated from a deposited layer of aluminum that is patterned and etched using conventional semiconductor fabrication techniques adapted to the spherical shape of the ball IC 110. The windings are insulated from each other by portions of the inter-level dielectric layer 1260. The actual number of individual windings of the coil may be far greater than the four specific windings 1229a, 1229b, 1229c and 1229d, shown. The ends of the coil 1229 are connected by additional conductors (not shown) to other circuit elements of the ball IC 110.

Referring now to FIG. 12B, there is illustrated an implementation of the transducer 1228. By way of example, the transducer 1228 may consist of a strain gauge fabricated atop the field oxide 1258, which strain gauge may be used to determine quantitative data related to pressure. A dome 1263 is supported at its periphery by the field oxide 1258, and defines a cavity 1265 between the dome 1263 and the field oxide 1258. The dome 1263 preferably comprises monocrystalline silicon and includes an elongated doped resistor 1267, which is indicated by the stippling at the outer surface of the silicon dome 1263. A dielectric layer 1269, such as silicon dioxide, overlies the dome 1263. Metal contacts 1271 and 1273 are formed over the dielectric layer 1269 and extend therethrough to make contact with the opposite ends of the doped resistor 1267. The metal contacts 1271 and 1273 have extensions (not shown in the cross section) that interconnect the doped resistor 1267 with circuitry of the previously described processor/control logic 140.

The strain gauge transducer 1228 can be fabricated by forming a layer of selectively etchable material in the shape of the cavity 1265 over the field oxide layer 1258. For example, a phosphorus-doped oxide can be deposited on the surface of the device, and then patterned into the desired shape by photolithographic techniques adapted to the spherical shape of the device. Next, the silicon dome 1263 is formed, such as by the deposition of polycrystalline silicon followed by recrystallization. Alternatively, the monocrystalline silicon layer used to make the dome 1263 can be epitaxially grown, such as by seeding the growth from an exposed portion of the substrate 1254 adjacent to the field oxide 1258. Such techniques are known, as described in U.S. Pat. No. 4,754,314, entitled "Split-Level CMOS," issued Jun. 28, 1988. A patterning procedure is then used to define the ultimate shape of the periphery of the dome 1263. Then, peripheral ports (not shown) are etched at opposite sides of the dome 1263 down to the doped oxide layer. Next, the device is exposed to an acid that preferentially etches doped oxide at a much faster rate than undoped silicon dioxide. It is well known that hydrofluoric acid will etch phosphorus doped oxide at a much faster rate (e.g., 15 times faster) depending on the phosphorus doping level and oxide density. The acid flows into the peripheral ports and etches the doped oxide layer laterally beneath the silicon dome 1263 to create the cavity 1265. The acid is then flushed out to introduce air or other gas, such as nitrogen, into the cavity 1265. Then, the outer dielectric layer 1269 is formed followed by the contacts 1271 and 1273. The deposition of the silicon dioxide of the dielectric layer 1269 fills the peripheral ports and seals the cavity 1265.

In a variation of the foregoing technique, a thin silicon nitride layer (not shown) can be deposited on the field oxide layer 1258 to serve as an etch-stop layer, followed by the deposition and patterning of the selectively etchable oxide layer. Optionally, another thin silicon nitride layer can be deposited atop the patterned oxide layer prior to the formation of the silicon layer 1263. These additional steps can facilitate preferential lateral etching of the patterned oxide layer to create a cavity like the cavity 1265, since hydrofluoric acid etches oxide at a much faster rate (e.g., 50 times faster) than silicon nitride.

In operation, the strain gauge 1228 senses pressure applied to the dome 1263 through the dielectric layers 1252 and 1269. As the pressure increases, the dome 1263 flexes downward very slightly, which also compresses the gas in the cavity 1265 to a slight degree. The resistance of the resistor 1267 varies in proportion to the variations in pressure of the fluid adjacent the outer surface 1256 of the dielectric layer 1252. The characteristics of semiconductor strain gauges are known in the art. A semiconductor strain gauge whose essential characteristics are similar to the strain gauge 1226 of FIG. 12B is described in U.S. Pat. No. 4,618,844, entitled "Semiconductor Pressure Transducer," issued Oct. 21, 1986, which is hereby incorporated by reference.

Other techniques may be used to integrate a pressure transducer 1228 onto the surface of a semiconductor ball 110. For example, variable capacitors, which are ideally suited for sensing pressure, can be fabricated using conventional semiconductor fabrication processes. A method of making a variable capacitor semiconductor transducer is described in U.S. Pat. No. 4,665,610, entitled "Method of Making a Semiconductor Transducer Having Multiple Level Diaphragm Structure," issued May 19, 1987, which is hereby incorporated by reference. Such a method or variations thereof can be adapted for fabrication on a spherical-shaped semiconductor substrate.

Referring now to FIG. 12C, there is illustrated a conventional strain gauge circuit according to the device structure of FIG. 12B. A conventional strain gauge architecture 1228 comprises a set of four resistances R1, R2, R3 and R4 in the configuration of a Wheatstone bridge. The resistances R1, R2, R3 and R4 are connected end-to-end in a loop such that the output signals are pulled off opposing nodes 1280 (a node common to resistances R1 and R2) and node 1282 (a node common to resistances R3 and R4). In like fashion, the excitation voltage is applied at the remaining two opposing nodes 1284 (the point common between resistances R1 and R4) and node 1286 (the point common to resistances R2 and R3). The excitation voltage is supplied by a power source 1288 placed across the nodes 1284 and 1286. In the context of FIG. 12B, the consolidation of resistances R1, R2, R3 and R4 represent the elongated doped resistor 1267 illustrated in FIG. 12B. The elongated doped resistor 1267 may be tapped off at various points to obtain the illustrated Wheatstone bridge. The metal contacts 1271 and 1273 of FIG. 12B relate to the output terminals 1290 and 1292 which interface with the processor 140. The power source 1288 may comprise a miniature self-contained battery system, as described hereinbelow, or may be provided externally from the control system 200 and coupled into the ball IC 110, and provided through voltage regulator 130 to the strain gauge transducer 1228 (similar to sensor 160). When under strain, the elongated doped resistor 1267 flexes such that resistance values R1, R2, R3 and R4 are changed in proportion to the changing condition sensed. The output at nodes 1290 and 1292 is a voltage which varies in direct relationship to the parameter being measured by the strain gauge transducer 1228.

Referring now to FIG. 12D, there is illustrated a portion of a ball IC 110', as modified from the embodiment of FIG. 12A, and using similar reference numerals which designate similar elements. The ball IC 110' includes a substrate 1254' on which a thick field oxide 1258' has been grown. Overlying the thick field oxide 1258' is a pressure transducer 1228' whose outer surface has been modified in accordance with a disclosed embodiment. The portion of dielectric layer 1252' lying over the transducer 1228' has recesses 1264 formed in its outer surface. These recesses 1264 may also extend beyond the edges of the transducer 1228' at least so far as the ball IC's 110' surfaces may be exposed to the measured medium.

The purpose of the recesses 1264 is to inhibit tissue adhesion to the surfaces of the ball IC 110' that are exposed to the patient's tissues, including liquids, such as blood. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion," TISSUE ENGINEERING, Vol. 2, No. 4, 1996 (available from the Dept. of Bioengineering, Clemson University, Clemson, S.C.). The recesses 1264 are presently preferred to be about one micron deep, three microns wide, and spaced three microns apart in a checkerboard topography. Such recesses can be fabricated by conventional selective etching techniques adapted to the spherical shape of the ball IC 110'.

Referring now to FIG. 13, there is illustrated a more detailed block diagram of an alternative embodiment having basic circuit functions of an external control system and a ball IC. Ball IC 1310 (similar to ball IC 110) includes an antenna/coil 1311, which serves the dual purpose of receiving signal energy from a control station 1320 and transmitting signal energy thereto. The signal energy may be received by the antenna/coil 1311 by inductive coupling if the control station 1320 is sufficiently close to the ball 1310. Alternatively, electromagnetic waves can be used to transmit power from the control station 1320 to the ball 1310, whereby the magnetic field component of the electromagnetic wave induces a current in the coil 1311 in accordance with known techniques. The power signal received by the antenna/coil 1311 is rectified and smoothed by a RF rectifier/smoother block 1312. The output of the rectifier block 1312 is connected to a DC power storage block 1313, such as a capacitor. Such capacitor might also perform a waveform smoothing function. A voltage regulator 1314 is used to make the DC voltage stable regardless of the distance between the control station 1320 and the ball 1310.

The ball 1310 includes a transducer block 1315 which represents both the function of sensing quantitative conditions, and the function of an actuator, such as an impulse generator, having anode and cathode portions of an electrode, and flanking electrodes. Such semiconductor electrical sensors and impulse generators are known in the art, and can be adapted to fabrication on a spherical semiconductor substrate, as described hereinabove. An analog-to-digital (A/D) converter 1305 is connected to the transducer 1315 to convert the electrical signal sensed by the transducer 1315 to a signal that can be transmitted out to the control station 1320. Notably, the converter 1305 can be part of the transducer 1315, such as a variable capacitor for generating a signal depending upon the variations in capacitance.

Control logic 1316, which can be part of an onboard processor that controls not only the converter 1305 but also circuitry on the ball 1310, is provided in accordance with known techniques. An RF oscillator 1317 generates an RF signal at a predetermined frequency in the RF band. An RF modulator 1318 modulates the output of the converter 1315 onto the carrier frequency signal. The resulting modulated signal is amplified by an RF amplifier 1319, and then transmitted to the antenna/coil 1311. The technique for transmitting data from the ball 1310 to the main control station 1320 using the carrier frequency generated by the RF oscillator 1317 can be in the form using any suitable modulation and protocol. For example, the modulation can be AM, FM, PM, FSK or any other suitable modulation technique. Further details of the preferred coil are described in the aforementioned commonly-assigned U.S. patent application Ser. No. 09/448,642 entitled "Miniature Spherical-Shaped Semiconductor With Transducer," and filed Nov. 24, 1999.

The external control station 1320 includes an antenna/coil 1321 that serves the dual purpose of generating the electromagnetic wave for transmitting power to the ball 1310, and receiving the RF data signal transmitted by the ball 1310. It is preferred that the frequency of the electromagnetic wave that is output by the antenna/coil 1321 is different from the carrier frequency generated by the RF oscillator 1317. An RF amplifier 1322 is used to couple the electromagnetic wave for power transmission to the antenna/coil 1321. An RF oscillator 1323 determines the frequency of the electromagnetic wave that is emitted by the control station 1320. The data received by the antenna/coil 1321 is detected by an RF detector 1324, and then amplified by an RF amplifier 1325. Preferably, the converter 1326 converts the signal from the RF amplifier 1325 to a digital signal, which in turn is input to a control logic block 1327. The control logic 1327 may be a smaller processor unit to interface with the main control station 1320. The control logic 1327 extracts the data from the signal received by the control station 1320 from the ball 1310, and displays that information on a suitable display 1328, such as a CRT screen.

Referring now to FIG. 14, there is illustrated a schematic block diagram of the control system and the ball IC for the powering/detection operation. The ball IC 1310, as described hereinabove, is operable to provide a transducer 1315 for interfacing with the desired quantitative condition. The illustrated embodiment of FIG. 14 is that associated with a "passive" system, which term refers to a system having no battery associated therewith. In order to operate the system, there is provided an inductive coupling element 1404 in the form of an inductor, which is operable to pick up an alternating wave or impulse via inductive coupling, and extract the energy therein for storage in the inductive element 1404. This will create a voltage across the inductive element 1404 between a node 1406 and a node 1408. A diode 1410 is connected between the node 1408 and the node 1412, with the anode of diode 1410 connected to node 1408 and the cathode of diode 1410 connected to a node 1412. Typically, the diode 1410 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1410 is operable to rectify the voltage across the inductive element 1404 onto the node 1412, which has a capacitor 1414 disposed between node 1412 and node 1406. Node 1412 is also connected through a diode 1416 having the anode thereof connected to node 1412 and the cathode thereof connected to a node 1418 to charge up a capacitor 1420 disposed between node 1418 and 1406. The capacitor 1420 is the power supply capacitor for providing power to the ball IC 1310. The capacitor 1414, as will be described hereinbelow, is operable to be discharged during operation of the system and, therefore, a separate capacitor, the capacitor 1420, is required for storing power to power the system of the ball IC 1310.

There is also provided a switching transistor 1431 which has one side of the gate/source path thereof connected to a node 1428 which is the output of the transducer 1315 and the other side thereof connected to a node 1432. The gate of transistor 1431 is connected to the output of the switch control 1430. Node 1432 is connected to the input of a buffer 1434 to generate an analog signal output thereof which is then converted with an A/D converter 1436 to a digital value for input to a CPU 1438. The CPU 1438 is operable to receive and process this digital input voltage. A clock circuit 1440 is provided for providing timing to the system. A memory 1439 is provided in communication with the CPU 1438 to allow the CPU 1438 to store data therein for later transmittal back to the remote location or for even storing received instructions. This memory 1439 can be volatile or it can be non-volatile, such as a ROM. For the volatile configuration, of course, this will lose all information when the power is removed. The CPU 1438 is operable to provide control signals to the switch control 1430 for turning on the transistor 1431 at the appropriate time. In addition to the transistor 1431 being toggled to read the transducer 1315, transistor 1431 could be a pass-through circuit such that the CPU 1438 can continually monitor the voltage at the output of the transducer 1315. System power to all power-consuming elements of the ball IC 1310 is provided at the SYSTEM PWR output node.

In order to communicate with the CPU 1438 for transferring data thereto and for allowing the CPU 1438 to transfer data therefrom, a receive/transmit circuit 1442 is provided for interfacing to node 1412 through a resistive element 1444. This allows RF energy to be transmitted to node 1412. It is important to note that the semiconductor junction across diode 1410 is a capacitive junction. Therefore, this will allow coupling from node 1412 to node 1408. Although not illustrated, this could actually be a tuned circuit, by selecting the value of the capacitance inherent in the design of the diode 1410. In any event, this allows an RF connection to be provided across diode 1410 while allowing sufficient energy to be input across conductive element 1404 to provide a voltage thereacross for rectification by the diode 1410 and capacitor 1414. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et. al., U.S. Pat. No. 3,944,982, entitled "Remote Control System For Electric Apparatus," issued Mar. 16, 1976, which are incorporated herein by reference. With these types of systems, power can continually be provided to the node 1412 and subsequently to capacitor 1420 to allow power to be constantly applied to the ball IC 1310.

The remote control system 1320 which is disposed outside of the body or away from the prosthesis and proximate to the ball IC 1310 includes an inductive element 1450 which is operable to be disposed in an area proximate to the skin, yet exterior to the body, in the proximity of the ball IC 1310, as close thereto as possible. The inductive element 1450 is driven by a driving circuit 1452 which provides a differential output that is driven by an oscillator 1454. This will be at a predetermined frequency and power level necessary to couple energy from inductive element 1450 to inductive element 1404. Since this is an external system, the power of the oscillator can be set to a level to account for any losses through the body tissues. To allow information to be transmitted, a modulation circuit 1456 is provided which is modulated by a transmitter signal in a block 1458 that allows information to be modulated onto the oscillator signal of the oscillator 1454, which oscillator signal is essentially a "carrier" signal. However, it should be understood that the information that is transmitted to the ball IC 1310 could merely be date information, whereas the CPU 1438 could operate independent of any transmitted information to provide the correct timing for the output pulses and the correct waveshape therefor. Alternatively, entire control of the system could be provided by the transmit signal 1458 and the information carried thereon, since power must be delivered to the illustrated embodiment due to the lack of any independent power in the ball IC 1310.

When the information is received from the ball IC 1310, it is superimposed upon the oscillator signal driving the inductive element 1450. This is extracted therefrom via a detector 1460 which has the output thereof input to a first low pass filter 1462, and then to a second low pass filter 1464. The output of low pass filters 1462 and 1464 are compared using a comparator 1466 to provide the data. The filter 1462 provides an average voltage output, whereas the filter 1464 provides the actual digital voltage output. The output of the comparator 1466 is then input to a CPU 1470 which also is powered by the oscillator 1454 to process the data received therefrom. This can then be input to a display 1472.

Figure 15A:
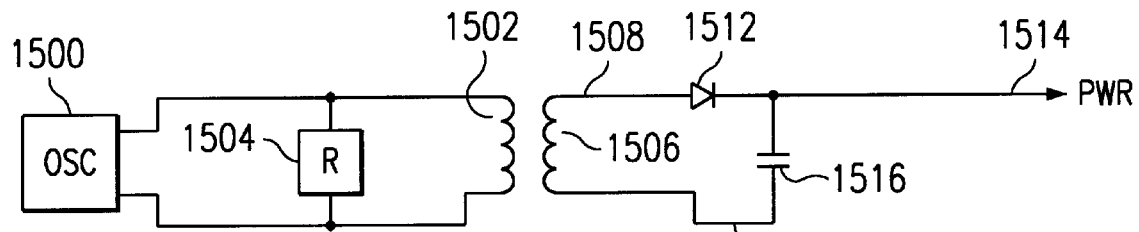
FIG. 15A illustrates an oscillator which drives an external inductive element.
Figure 15B:
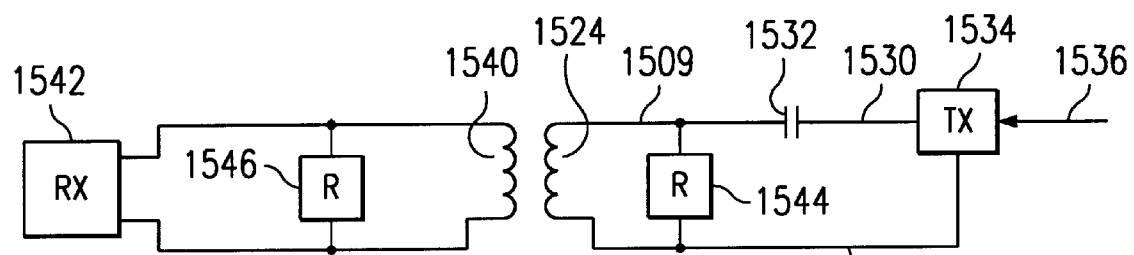
FIG. 15B illustrates the receive operation which utilizes a separate inductive element or antenna in the ball IC.
Figure 15C:
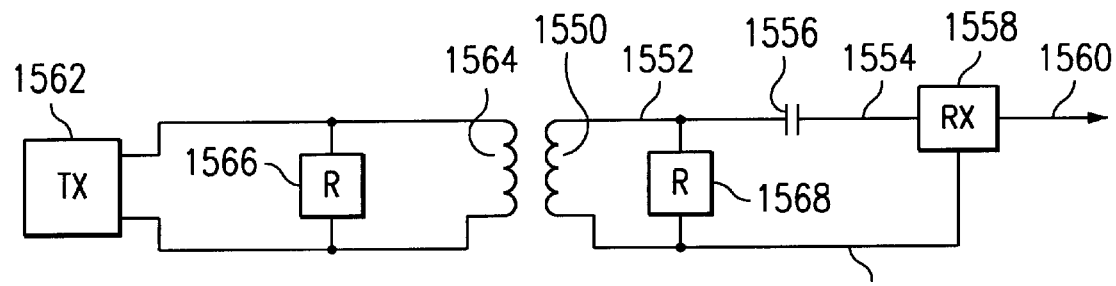
FIG. 15C illustrates a simplified schematic diagram of the receive portion.

Referring now to FIGS. 15A–15C, there are illustrated alternate embodiments for the transmit/receive operation. In FIG. 15A, there is provided an oscillator 1500 which drives an external inductive element 1502. Typically, there is some type of load 1504 disposed across the inductive element 1502. This is the primary power that is provided to the system. A separate inductive element 1506 is provided on the ball IC 1310, for being inductively coupled to the inductive element 1502. Thereafter, a voltage is generated across the inductive element 1506, the inductive element 1506 being connected between nodes 1508 and 1510. A diode 1512 is connected between node 1508 and a power node 1514, and a power supply capacitor 1516 is disposed across node 1514 and a node 1510. This allows the voltage on node 1508 to be rectified with diode 1512.

In FIG. 15B, the receive operation. in this alternative embodiment, utilizes a separate inductive element or antenna 1524 in the ball IC 1310, which is operable to be connected between nodes 1509 and 1511. Node 1509 is capacitively coupled to a transmit node 1530 with a capacitor 1532, the capacitor 1532 being a coupling capacitor. A transmitter 1534 is provided for transmitting received data from a line 1536 to the node 1530, which is then coupled to the node 1509 to impress the RF signal across the inductive element 1524.

A corresponding inductive element 1540 is disposed on the external remote controller of control system 1320, which inductive element 1540 is operable to be disposed proximate to the inductive element 1524, but external to the human body. The inductive element 1540 is basically a "pick-up" element which is operable to receive information and function as an antenna, and provide the received signal to a receiver 1542. The structure of FIG. 15B is a separate structure, such that node 1509 is isolated from node 1508, the power receiving node. However, it should be understood that any harmonics of the oscillator 1500 would, of course, leak over into the inductive element 1524. This can be tuned out with the use of some type of tuning element 1544 on the ball IC 1310 disposed across inductive element 1524, and also a tuning element 1546 disposed across the inductive element 1540, i.e., the antenna.

Referring now to FIG. 15C, there is illustrated a simplified schematic diagram of the receive portion. The ball IC 1310 has associated therewith a separate receive antenna or inductive element 1550 disposed between node 1513 and a node 1552. Node 1552 is capacitively coupled to a receive node 1554 with a coupling capacitor 1556. A receiver 1558 is provided for receiving the information transmitted thereto and providing on the output thereof data on a data line 1560. The receiver 1558 is operable to receive the RF signal, demodulate the data therefrom, and provide digital data on the output 1560. External to the human body and the ball IC 1310 is a transmitter 1562 which is operable to impress a signal across an external inductive element 1564. The inductive element 1564 basically provides the RF energy and is essentially tuned with a tuning element 1566. A corresponding tuning element 1568 is provided on the ball IC 1310 and disposed across inductive element 1550, the inductive element 1550 acting as an antenna, as well as the inductive element 1564.

Note that in circumstances where the signals of ball IC 1310 cannot be adequately received therefrom and/or power coupled thereto, the external location system 1320 may need to be inserted into the body proximate to the ball IC 1310 in order to couple the transmit/receive signals and power. Furthermore, where more than one ball 1310 is used, communication of power and data signals between the various ball ICs 1310 may need to employ distinct time periods (i.e., time multiplexing) when communication occurs using a single common frequency, or discrimination circuits may need to be used where communication occurs simultaneously with the plurality of implanted ball ICs 1310 having different oscillator frequencies.

Referring now to FIG. 16, there is illustrated a side view of an alternative embodiment utilizing additional circuitry or structure attached to the ball IC 1310 for providing a local power source. As described hereinabove, the ball IC 1310 requires a power-generating structure for storing a power supply voltage such that diodes must be provided for receiving and rectifying a large amount of power and charging up a power supply capacitor. Alternatively, the ball IC 1310 could be configured to interface to an attached power supply system 1600 comprising either a battery or a capacitor. The local power supply system 1600 is illustrated as disposed on a circuit board 1603 defined by supporting structures 1602 and 1604. The circuit board 1603 contains electronics for interfacing the local power supply system 1600 to the ball IC 1310.

Referring now to FIG. 17, there is illustrated a schematic block diagram of the ball IC 1310 using a battery as the local power supply system 1600. A battery 1701 is provided as a source of self-contained power and is connected across a capacitor 1700 to provide smoothing of any power output to the system power-consuming elements of the ball IC 1310. Power for all onboard components is obtained from the SYSTEM POWER output by providing sufficient charge to the capacitor 1700. The capacitor 1700 could be formed on the surface of the ball IC 1310 or it could actually be part of the battery structure 1701. Additionally, the capacitance 1700 could actually be the capacitance of the battery 1701. Additional structure could be provided for powering the CPU 1438 and the other circuitry on the ball IC 1310 from the battery 1701. As such, there would only be required a smaller inductive element 1702 and a capacitor 1704 to allow the receive/transmit block 1442 to receive/transmit information from and to the remote exterior control station 1320. The switch control 1430 controls the gate of the switching transistor 1431 to switch output of the transducer 1315 through the switching transistor 1431 source/drain path to the CPU 1438.

Referring now to FIG. 18, there is illustrated a perspective view of the ball IC 1310, wherein the inductive element 1404 (similar to inductive element 120) is as being strips of conductive material wrapped around the exterior of the ball IC 1310. The inductive element 1404 is formed of a conductive strip wrapped many times around the ball IC 1310. The length of inductive element 1404 depends upon the receive characteristics that are required. As described hereinabove with reference to FIGS. 15A–15C, there could be multiple conductive strips, one associated with a receive function, another for a transmit function, and another for a power function, or they could all share one single conductive element or strip. Notably, the inductive strips would be disposed on one side of the ball IC 1310 for communication purposes.

On one end of the ball IC 1310 there is provided a transducer interface 1800 of the transducer 1315 having, optionally, one or more interface balls 1802 (or partial balls, called nodules) associated therewith extending from the transducer interface surface to provide enhanced engagement of the measuring surface or physical entity. The interface balls 1802 can be made of non-reactive material, e.g., gold to prevent degradation while in the body. Note that in some applications, the interface nodules 1802 are not required for obtaining the desired quantitative data. On the other end of the ball IC 1310 are provided interconnect balls 1804 (or nodules) for interconnecting to one or more other spherical balls, as described hereinabove, which may provide similar functions such as monitoring of quantitative data, or unique functions such as supplying only power or data buffering and storage.

Referring now to FIG. 19, there is illustrated a cross-sectional diagram of the surface of the ball IC 1310 illustrating the conductive strips forming the inductive element 1404. The conductive strips are referred to by reference numeral 1910 which are spaced above the surface of the integrated circuit of the ball IC 1310 by a predetermined distance, and separated therefrom by a layer of silicon dioxide. A passivation layer 1911 is then disposed over the upper surface of the conductive strips 1910. The conductive strips 1910 can be fabricated from polycrystalline silicon but, it would be preferable to form them from the upper metal layer to result in a higher conductivity strip. This will allow the strips 1910 to be narrower and separated from each other by a larger distance. This separation would reduce the amount of capacitance therebetween.

One end of the strips 1910 is connected to a diode structure 1913. The diode structure 1913 is formed of an N-well implant region 1914 into which a P-well implant region 1916 is disposed, and an N-well implant region 1918 disposed within the P-well implant region 1916. This forms a PN diode where one end of the conductive strips 1910, a conductive connection 1920, is connected to the P-well 1916 implant region, and a conductive layer 1922 is connected at one end to the N-well implant region 1918. This conductive layer or strip 1922 extends outward to other circuitry on the integrated circuit and can actually form the capacitor. Since it needs to go to a capacitor directly, a lower plate 1924 formed of a layer of polycrystalline silicon or metal in a double-metal process, could be provided separated therefrom by a layer of oxide.

In another application, the sensor ball is used to stimulate excitable tissue. The semiconductor ball can function as a TENS (Transcutaneous Electrical Nerve Stimulator) unit. This is very important in treating chronic pain syndromes. The unit can also be used to stimulate both nerve and muscles in paralyzed or injured limbs to help prevent the development of atrophy or as a means to reduce the inflammatory response. Multiple balls which function as both receivers of electrical signal and also as transmitters of signal could function as a bridge between an amputated limb and a moveable prosthetic "hand."

Figure 20:
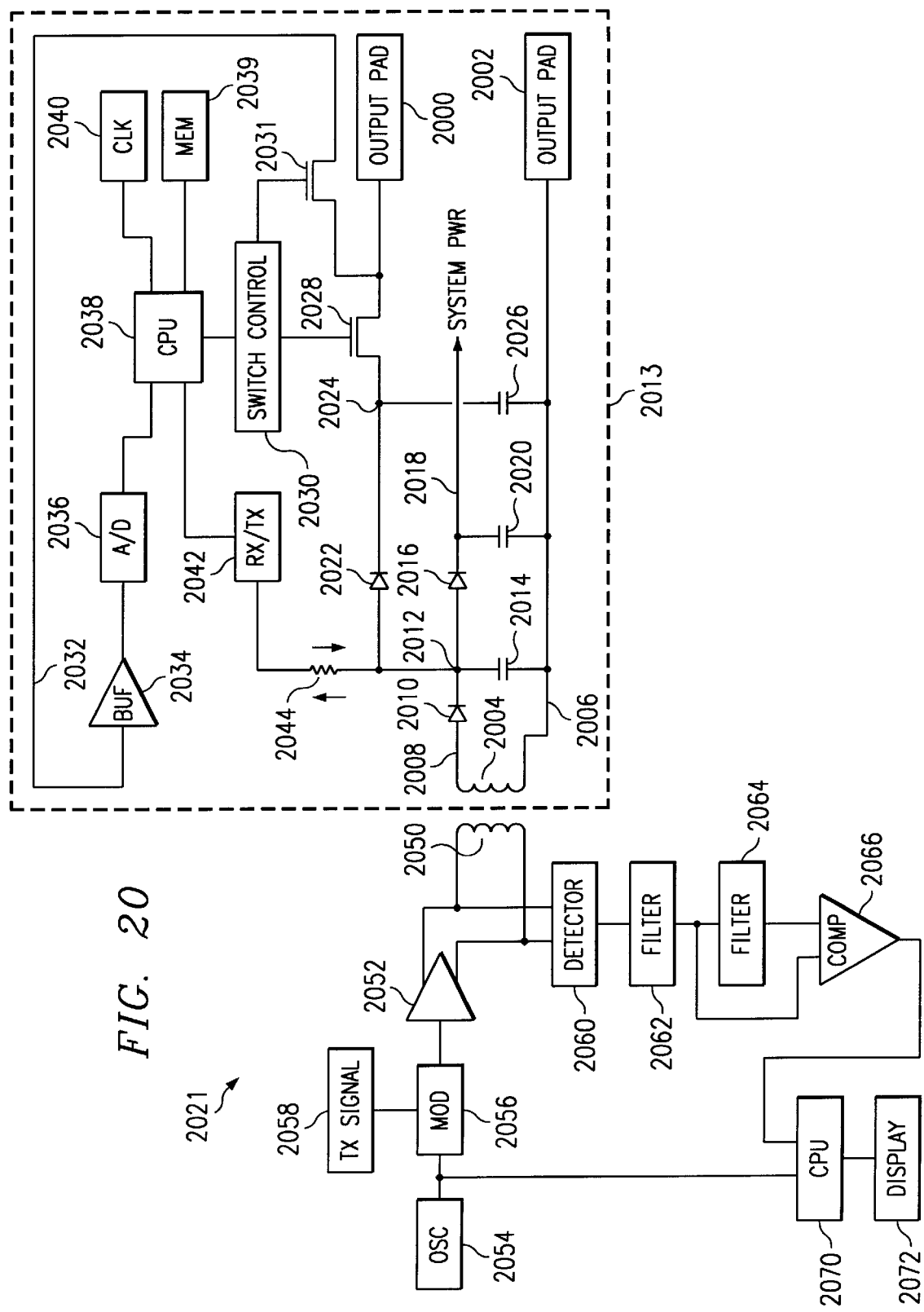
FIG. 20 illustrates a schematic block diagram of the ball IC in an actuator function and the remote control system for the powering/detection operation.

Referring now to FIG. 20, there is illustrated a schematic block diagram of the ball IC in a stimulus function and the remote control system for the powering/detection operation. A ball IC 2013 (similar to ball 1310) is operable to provide two contact interfaces, an output pad 2000 as an anode and an output pad 2002 as a cathode, for interfacing with the desired medium. The spacing between these two pads or contacts 2000 and 2002 is approximately 0.5 cm. The illustrated embodiment of FIG. 20 is that associated with a "passive" system, which term refers to the fact that there is no battery associated therewith. In order to operate the system, there is provided an inductive coupling element 2004 in the form of an inductor, which is operable to pick up an alternating wave or impulse via inductive coupling and extract the energy therein for storage in the inductive element 2004. This will create a voltage across the inductive element 2004 between a terminal 2006 and a terminal 2008. A diode 2010 is connected between the node 2008 and a node 2012, with the anode of diode 2010 connected to node 2008 and the cathode of diode 2010 connected to a node 2012. Typically, the diode 2010 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 2010 is operable to rectify the voltage across the inductive element 2004 onto the node 2012, which has a capacitor 2014 disposed between node 2012 and node 2006. Node 2012 is also connected through a diode 2016 having the anode thereof connected to node 2012 and the cathode thereof connected to a node 2018 to charge up a capacitor 2020 disposed between node 2018 and 2006. The capacitor 2020 is the power supply capacitor for providing power to the ball IC 2013. The capacitor 2014, as will be described hereinbelow, is operable to be discharged during operation of the system and, therefore, a separate capacitor, the capacitor 2020, is required for storing power to power the ball system 2013.

The node 2012 is connected to the anode of a diode 2022, the cathode thereof connected to a node 2024. A main capacitor 2026 is connected between node 2024 and node 2006. The capacitor 2026, as will be described hereinbelow, is operable to provide the primary discharge energy to the desired medium via the output pad 2000, the anode of the ball IC 2013. This node 2024 is connected to one side of the gate/source path of a drive transistor 2028, the other side thereof connected to the output pad 2000. The gate of drive transistor 2028 is connected to the output of a switch control circuit 2030. Drive Transistor 2028 is operable to be turned on for a short period of time to connect to the top plate of capacitor 2026 to the output pad 2000 and subsequently, to conduct current to the desired medium.

In addition to transmitting energy out on output pad 2000, there is also provided a sense transistor 2031 which has one side of the gate/source path thereof connected to the output pad 2000 and the other side thereof connected to a node 2032. The gate of sense transistor 2031 is connected to the output of the switch control 2030. Node 2032 is connected to the input of a buffer 2034 to generate an analog signal output thereof which is then converted with an A/D converter 2036 to a digital value for input to a CPU 2038. The CPU 2038 is operable to receive and process this digital input voltage. A clock circuit 2040 is provided for providing timing to the system. A memory 2039 is provided in communication with the CPU 2038 to allow the CPU 2038 to store data therein for later transmittal back to the remote location or for even storing received instructions. This memory 2039 can be volatile or it can be non-volatile, such as a ROM. For the volatile configuration, of course, this will lose all information when the power is removed.

The CPU 2038 is operable to provide control signals to the switch control 2030 for turning on the drive transistor 2028 or the sense transistor 2031 at the appropriate time. Typically, the drive transistor 2028 is controlled to turn on for a period of approximately 0.5 microseconds 60–80 times per minute. Once drive transistor 2028 is turned off, then sense transistor 2031 can be turned on. Alternatively, sense transistor 2031 could be a pass-through circuit such that the CPU 2038 can always monitor the voltage on the output pad 2000. However, it is desirable with the sense transistor 2031 and the sensing operation to sense depolarization in the desired medium after an output voltage has been provided thereto for a short duration of time. The output pad 2002 provides the return path of the stimulus current.

In order to communicate with the CPU 2038 for transferring data thereto and for allowing the CPU 2038 to transfer data therefrom, a receive/transmit circuit 2042 is provided for interfacing to node 2012 to a resistive element 2044. This allows RF energy to be transmitted to node 2012. It is important to note that the semiconductor junction across diode 2010 is a capacitive junction. Therefore, this will allow coupling from node 2012 to node 2004. Although not illustrated, this could actually be a tuned circuit, by selecting the value of the capacitance inherent in the design of the diode 2010. In any event, this allows an RF connection to be provided across diode 2010 while allowing sufficient energy to be input across conductive element 2004 to provide a voltage thereacross for rectification by the diode 2010 and capacitor 2014. Typically, the operating frequency of this connection will be in the MHz range, depending upon the design of which a variety are possible. For example, some of these are illustrated in Beigel, U.S. Pat. No. 4,333,072, entitled "Identification Device," issued Jun. 1, 1982, and Mogi et. al., U.S. Pat. No. 3,944,982, entitled "Remote Control System For Electric Apparatus," issued Mar. 16, 1976, which are referenced hereinabove. With these types of systems, power can continually be provided to the node 2012 and subsequently to capacitors 2020 and 2026 to allow power to be constantly applied to the epicardial lead. The diode 2022 may not be required in order to provide the sufficient charge to capacitor 2026, but some type of isolation is required between the capacitor 2026 and the capacitor 2020. Voltage regulation may also be required in order to provide a shaped pulse on the output pad 2000. This could be provided by the switch control 2030.

A remote system 2021 which is disposed external to the body and proximate to the ball IC 2013, includes an inductive element 2050 which is operable to be disposed in an area proximate to the skin, exterior to the body, and in the proximity of the ball IC 2013. The inductive element 2050 is driven by a driving circuit 2052 which provides a differential output that is driven by an oscillator 2054. This will be at a predetermined frequency and power level necessary to couple energy from inductive element 2050 to inductive element 2004. Since this is an external system, the power of the oscillator can be set to a level to account for any losses through the body tissues. To allow information to be transmitted, a modulation circuit 2056 is provided which is modulated by a transmitter signal in a block 2058 that allows information to be modulated onto the oscillator signal 2054, which oscillator 2054 provides a "carrier" signal. However, it should be understood that the information that is transmitted to the ball IC 2013 could merely be date information whereas the CPU 2038 could operate independent of the information being transmitted to provide the correct timing and waveshape for the output pulses. Alternatively, the entire control of the system may be provided by the transmit signal 2050 and the information carried thereon, because power must be delivered to the illustrated embodiment when there is a lack of an independent power source in the ball IC 2013.

The information received from the ball IC 2013 is modulated upon the oscillator signal driving the inductive element 2050. This information is extracted therefrom via a detector 2060 which has the output thereof input to a first low pass filter 2062 and then to a second low pass filter 2064. The output of low pass filters 2062 and 2064 are compared with a comparator 2066 to provide the data. The filter 2062 will provide an average voltage output, whereas the filter 2064 will provide the actual digital voltage output. The output of the comparator 2066 is then input to a CPU 2070 which also is powered by the oscillator 2054 to process the data received therefrom. This can be input to a display 2072.

Figure 21A:
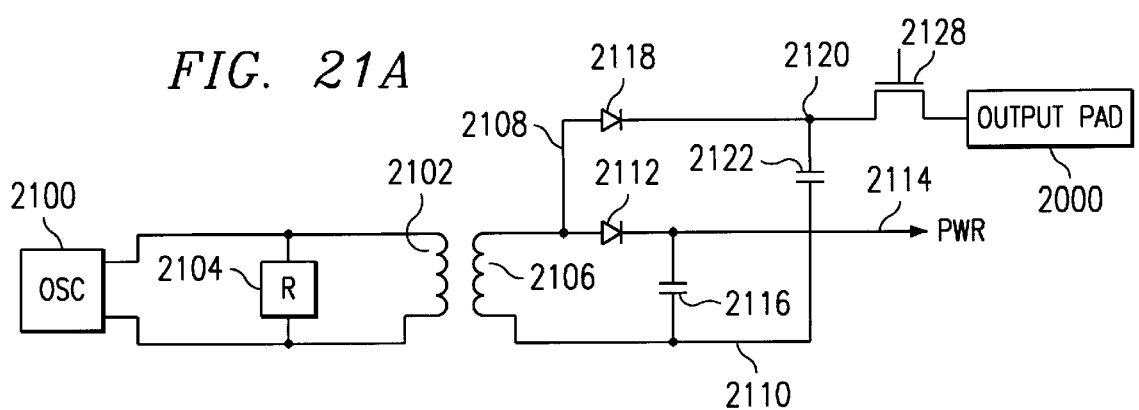
FIG. 21A illustrates an oscillator which drives an external inductive element of an actuator embodiment.
Figure 21B:
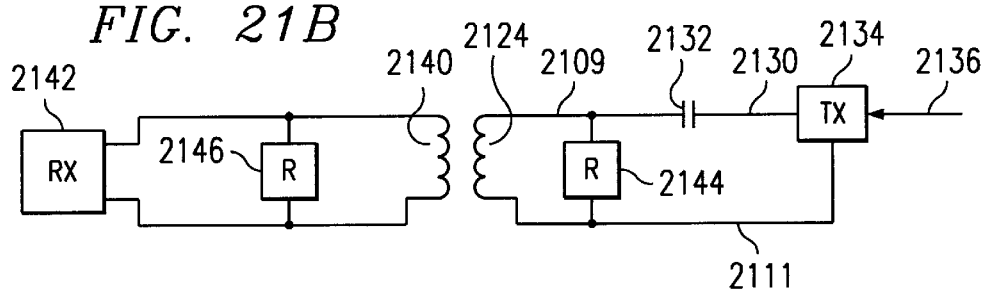
FIG. 21B illustrates a receive operation which utilizes a separate inductive element or antenna in the ball IC.
Figure 21C:
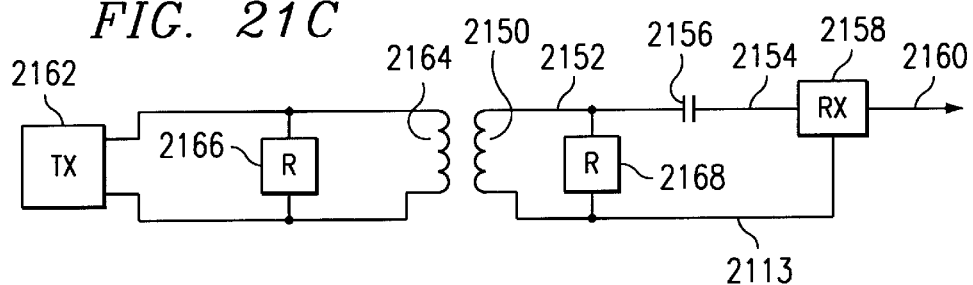
FIG. 21C illustrates a simplified schematic diagram of the receive portion of an actuator function.

Referring now to FIGS. 21A–21C, there are illustrated alternate embodiments for the transmit/receive operation of ball IC when functioning as an actuator. In FIG. 21A, there is provided an oscillator 2100 which drives an external inductive element 2102 which may be utilized to couple both electrical power and information or data. Typically, there is some type of load 2104 disposed across the inductive element 2102. A separate inductive element 2106, inductively coupled to inductive element 2102, is provided on the ball IC 2013 of FIG. 20. Voltage generated across the inductive element 2106, and connected between a node 2108 and a node 2110, is applied across rectifier 2112, which is connected between node 2108 and a power node 2114. A power supply capacitor 2116 disposed across node 2114 and node 2110 stores the rectified voltage for use by the circuit. Similarly, a rectifier 2118 is connected between the node 2108 and a node 2120 which is connected to one side of a main "surge" capacitor 2122. The other side of capacitor 2122 is connected to node 2110. This capacitor 2122 is similar to the main "surge" capacitor 2026 in FIG. 20. The switch transistor 2128 is provided for connecting the node 2120 to the output pad 2000.

The receive operation in the embodiment illustrated in FIG. 21B utilizes a separate inductive element or antenna 2124 in the ball IC 2013, which is operable to be connected between nodes 2109 and 2111. Node 2109 is capacitively coupled to a transmit node 2130 with a capacitor 2132, the capacitor 2132 being a coupling capacitor. A transmitter 2134 is provided for transmitting received data from a line 2136 to the node 2130 which is then coupled to the node 2109 to impress the RF signal across the inductive element 2124.

A corresponding inductive element 2140 is disposed on the external remote controller, which inductive element 2140 is operable to be disposed proximate to the inductive element 2124 for inductive coupling therewith, but external to the body having the ball 2013 implanted therein. The inductive element 2140 operates as a "pick-up" element to receive information, i.e., to function as an antenna, providing the received signal to a receiver 2142. The structure of FIG. 21B is a separate structure, such that node 2109 is isolated from node 2108, the power receiving node illustrated in FIG. 21A. However, it should be understood that harmonics of the oscillator 2100 may be coupled into the inductive element 2124. These harmonics may be tuned out by using a tuning element 2144 on the ball 2013 disposed across inductive element 2124, and also a tuning element 2146 disposed across the inductive element 2140, i.e., the antenna.

Referring now to FIG. 21C, there is illustrated a simplified schematic diagram of the transmit embodiment. The ball 2013 has associated therewith a separate receive antenna, shown as an inductive element 2150, disposed between a node 2110 and a node 2152. Node 2152 is capacitively coupled to a receive node 2154 with a coupling capacitor 2156. A receiver 2158 is provided for receiving the information transmitted thereto and providing on the output thereof data on a data line 2160. The receiver 2158 is operable to receive the RF signal, demodulate the data therefrom, and provide digital data on the output 2160. External to the human body having the ball 2013 implanted therein is a transmitter 2162 that is operable to impress a signal across an external inductive element 2164. The inductive element 2164, tuned with a tuning element 2166, basically provides for coupling the RF energy with inductive element 2150. A corresponding tuning element 2168 is provided on the ball 2013 and disposed across inductive element 2150. The inductive element 2150 and the inductive element 2164, one being inside the body and the other being external to the body, function as the antennae for coupling RF signal energy across the interface between the ball 2013 and the control system 2021.

Figure 22:
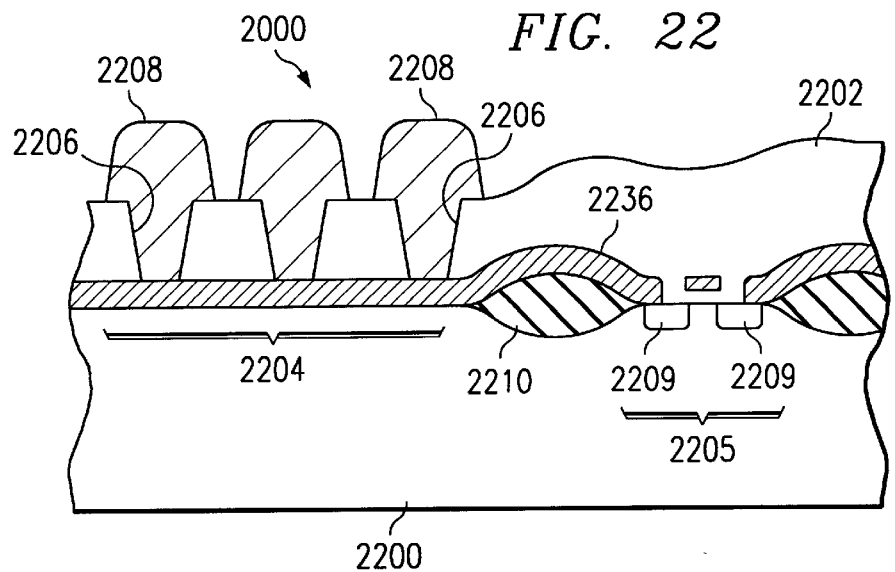
FIG. 22 illustrates a cross-sectional view of the output pad 2000 of FIG. 20.

Referring now to FIG. 22, there is illustrated a cross-sectional view of the output pad 2000 of FIG. 20. In general, the output pad 2000 is required to provide a conductive interface between the transistor 2028 (similar to transistor 2128) and the desired medium. This therefore requires some type of metallic interface that is non-reactive. Such an interface would require a metal such as gold, platinum and the like. In the disclosed embodiment, gold would be provided. After the formation of the upper metal layer 2236 via a deposition technique with metal such as aluminum or copper, a passivation layer of oxide 2202 is deposited to basically prevent oxidation of the metal layer 2236, and protect the semiconductor circuits, in general. The metal contact layer 2236 extends beyond the active region 2205 to an output pad region 2204, and is separated from the active region 2205 by a layer of field oxide 2210 or some type of isolation oxide. There may be some type of channel stop implant disposed below the, field oxide layer 2210. The metal contact layer 2236 extends from the source/drain implant 2209 to the region 2204. This metal contact layer 2236 is required to be fairly conductive. Typically, polycrystalline silicon is not of sufficient conductivity to meet this requirement. Therefore, some type of polysilicide process may be required, wherein the upper surface is converted to some type of silicide such as titanium disilicide to lower the surface resistivity thereof. Alternatively, a metal layer could be provided which is connected to the metal contact region 2236.

Once the contact region 2236 is formed, and the passivation layer 2202 is disposed over the entire structure, vias 2206 are formed therein. These vias 2206 are then filled with metallic plugs 2208 by forming a layer of metal over the oxide passivation layer 2202 and then etching the passivation layer 2202 to remove the undesired portions. The metal plugs 2208 may be formed of metal such as aluminum or gold. If they were formed of gold, this would allow for soldering if they were to be used as contacts. However, in this context, these plugs 2208 are utilized for conductivity purposes. Therefore, an aluminum plug would be sufficient if it were covered with a thin layer of gold to render the aluminum non-reactive and prevent oxidation thereof. Alternatively, in the disclosed embodiment, the plug may, of course, be gold. However, it should be understood that any type of non-reactive metal could be utilized as long as the surface thereof is sufficiently non-reactive and the conductance of the plug 2208 is sufficiently high to result in a low resistance path between the exterior of the spherical ball IC and a capacitive plate of the capacitor 2026. The reason for this is that the stored charge must be discharged into a resistance as low as 500 Ohms, and any significant resistance disposed between the upper plate of the capacitor 2026 and the exterior must be minimized.

Figure 23:
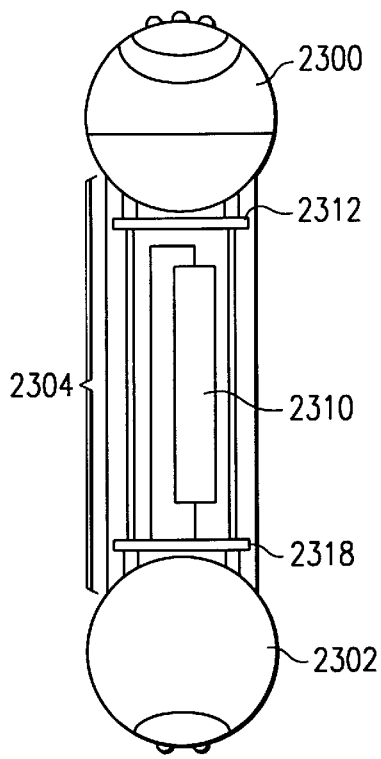
FIG. 23 illustrates a side view of an alternate embodiment of the actuator or stimulus function.

Referring now to FIG. 23, there is illustrated a side view of an alternate embodiment of the actuator or stimulus function. In one application, a stimulus embodiment requires two primary ball IC structures (2300 and 2302), and a power supply generating structure 2304 for storing a power supply voltage. Diodes must be provided for receiving and rectifying a large amount of power and charging up a power supply capacitor, in addition to a main "surge" capacitor, for providing a relatively large amount of pulsed energy to the desired medium when in the stimulus configuration. The space between the spherical IC 2300 and the spherical IC 2302 may contain either a battery or a capacitor represented by a structure 2310. This is disposed between a supporting structure having supporting ends 2312 and 2318 which interface to the ball IC structures 2300 and 2302, respectively.

Figure 24:
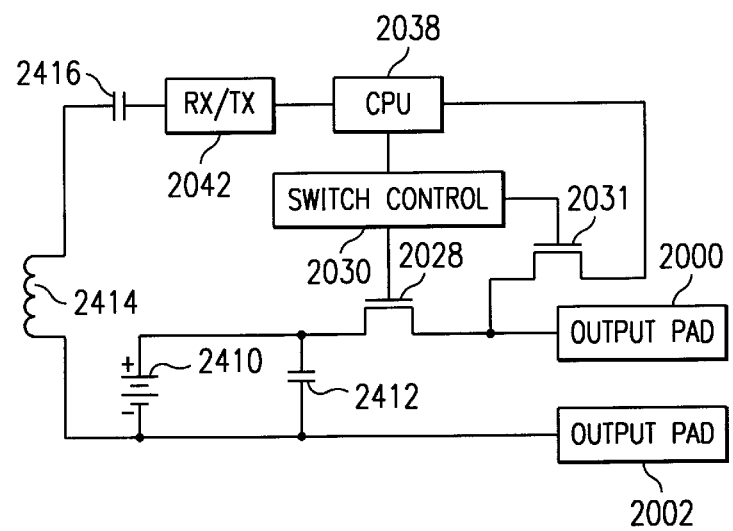
FIG. 24 illustrates a schematic block diagram of the actuator of FIG. 23 illustrating the use of a battery.

Referring now to FIG. 24, there is illustrated a schematic block diagram of the actuator of FIG. 23 illustrating the use of a battery. A battery 2410 is provided which is connected to a capacitor 2412. The capacitor 2412 could be identical to the capacitor 2026 of FIG. 20 in that it could be formed on the surface of the spherical IC 2013, or it could actually be part of the battery structure 2310 shown in FIG. 23. The battery 2410 is placed across the capacitor 2412 to provide sufficient charge therefor. Additionally, the capacitance 2412 could actually be the capacitance of the battery 2410. Additional structure could be provided for powering the CPU 2038 and the other circuitry on the chip from the battery 2410. As such, there would only be required a smaller inductive element 2414 and a capacitor 2416 to allow the receive/transmit block 2042 to receive/transmit information from and to the remote exterior station. The CPU 2038 is operable to provide control signals to the switch control 2030 for turning on the drive transistor 2028 or the sense transistor 2031 at the appropriate time. Typically, the drive transistor 2028 is controlled to turn on for a period of approximately 0.5 microseconds 60–80 times per minute. Once drive transistor 2028 is turned off, then sense transistor 2031 can be turned on. Alternatively, sense transistor 2031 could be a pass-through circuit such that the CPU 2038 can always monitor the voltage on the output pad 2000. However, it is desirable with the sense transistor 2031 and the sensing operation to sense depolarization in the desired medium after an output voltage has been provided thereto for a short duration of time. The output pad 2002 provides the return path of the stimulus current. It is to be appreciated that the sensor embodiment depicted in FIGS. 16–24 and described hereinabove, is illustrative of both sensor and actuator functions of transducers which may be provided using the spherical semiconductor IC technology of the present disclosure.

Computerized Data Processing

Diagnosis, medical record keeping, hospital information systems and community health-care facilities pose several problems involving pattern recognition, complex systems, human interaction, and economics. Many of these problems can be simplified by automation so as to allow these variables to be more easily monitored. The ball of this invention can greatly simplify these problems. In one example, the inventive ball can serve as a miniature information databank pertaining to an orthopedic surgical implant, or orthopedic surgical procedure. Automated patient information retrieval from the implanted device or affected tissue allows comprehensive and reliable patient information to be immediately accessed as needed.

In one embodiment of such a miniature information databank, a spherical-shaped IC of this invention can be located in the gluteus maximus of a male patient. The IC is coded with patient medical information and/or vital statistics. Information such as allergy of a patient to penicillin or a heart condition can be coded into spherical-shaped IC and retrieved from outside the body by interrogation by a source. The source can be located in the admission or emergency room of a hospital, a doctor's office or other location. Alternatively, it can be portably carried in the ambulance, with a doctor or paramedic or other medical personnel. Interrogation of the spherical-shaped IC with coded patient history information allows immediate retrieval of patient history for use in diagnosis and treatment of the orthopedic patient in emergency conditions. Such information can also be valuable in non-emergency conditions since it can provide information about a patient that may not otherwise be available. For instance, when a patient is seeing a new doctor, the IC can provide a databook of health information that can be retrieved by a doctor on command. This allows for a quicker, more complete initial exam and results in a more informed diagnosis. While forms currently in use by doctor offices and completed by a new patient provide the same information, such information is only as good as a person's recollection. In one embodiment, the ball provides an automated databank of this information that provides a complete, accurate record of this information independent of a patient's recollection.

In another embodiment, the ball of this invention is coded with a person's vital statistics. Such statistics could include name, social security, address and phone number and who to contact in case of an emergency. Should a person become unconscious, as a result of an accident, for example, an interrogation of the ball could immediately provide information vital in identifying the person, and also who to contact as the next of kin. Such information is invaluable in determining what assistance an unconscious person may require. Should a person die in war, accident, natural causes or otherwise, such information allows for immediate identification of the person and means for notifying the next of kin. In addition, should a child become lost, for example, interrogation of an IC containing this kind of information provides information helpful in finding the parents of the lost child.

In any of these embodiments, privacy of the coded information is always a concern. The coded information may contain personal information intended for access only by persons such as doctors, paramedics or others who have been granted appropriate authorization. To protect the privacy of the coded information, the information retrieval system will only allow for detection at very finite distances such as up to 5–10 cm. This will help maintain an individual's confidentiality. In addition, spherical-shaped IC may also be coded with a unique device security ID. This ID would serve as a "key" without which IC could not be unlocked by an interrogator. Consequently, only authorized personnel with the knowledge of ID would be able to unlock IC and initiate transmission of a data stream of information from the spherical-shaped IC. In this way, the process of information is produced since no data stream of information from the ball semiconductor IC can be initiated without first unlocking the transmission channel of IC using appropriate security information.

Figure 25:
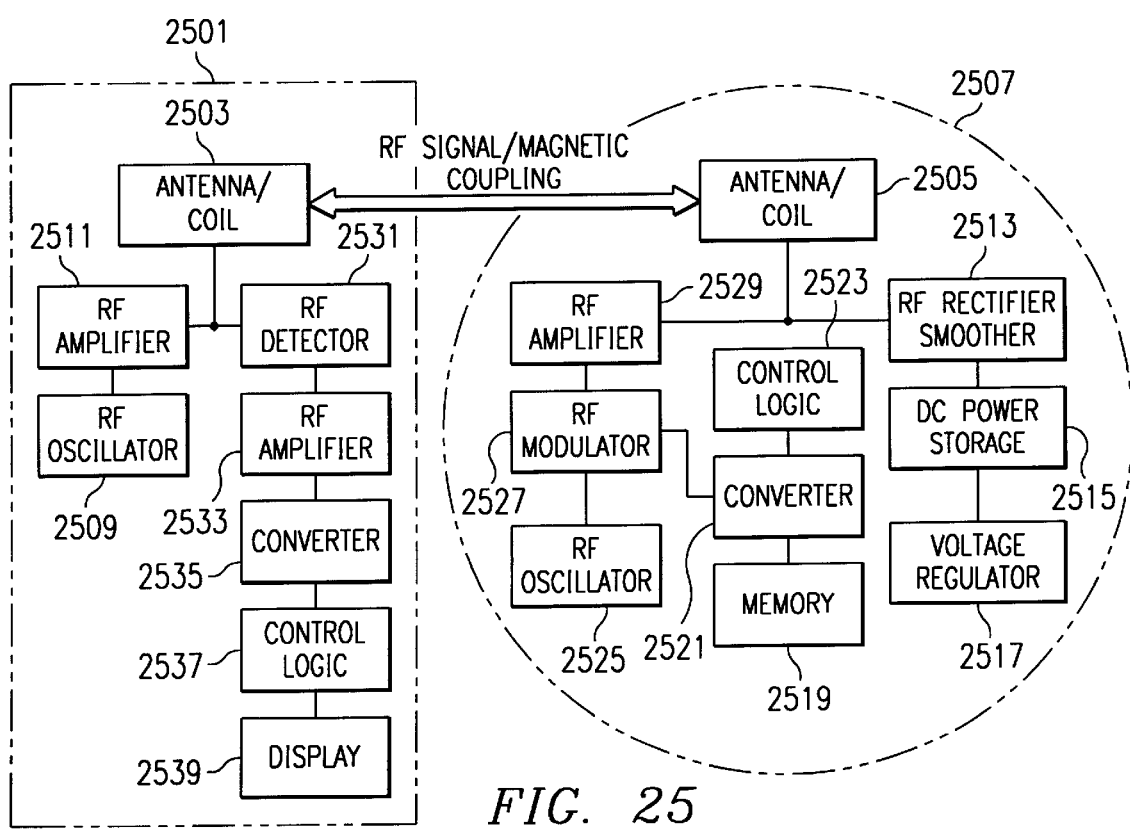
FIG. 25 illustrates a detailed block diagram of an alternative embodiment of the ball IC/control system where the ball IC has a memory function, according to the disclosed architecture.

Referring now to FIG. 25, there is illustrated a detailed block diagram of an alternative embodiment of the ball IC/control system where the ball IC has a memory function, according to the disclosed architecture. A control unit 2501 (similar to control system 2021) includes an antenna/coil 2503 that transmits RF power to an antenna/coil 2505 of a ball IC 2507 (similar to ball IC 2013). Power is transported either by RF radiation or by magnetic coupling between antenna coil 2503 and antenna coil 2505. Control unit 2501 generates RF power with an RF oscillator 2509 coupled to an RF amplifier 2511. The RF amplifier 2511 is coupled to antenna/coil 2503. The RF power received at antenna/coil 2505 of ball 2507 is rectified and smoothed by an RF rectifier smoother 2513 coupled to antenna/coil 2505. RF rectifier smoother 2513 converts RF energy to a DC voltage. DC power is stored in a DC power storage unit 2515, which preferably includes a capacitor. The capacitor of DC power storage unit 2515 may be included in the smoothing portion of the RF rectifier smoother 2513. A voltage regulator 2517 is coupled to DC power storage unit 2515. Voltage regulator 2517 makes the DC voltage powering ball 2507 stable for any condition or distance between control unit 2501 and ball 2507. Voltage regulator 2517 supplies DC voltage to all circuits of ball 2507 in a manner well known to those skilled in the art. Ball 2507 includes a non-volatile memory 2519, which is programmed with identifying information. The output from memory 2519 is converted to an RF signal by a converter 2521. A control logic 2523 controls converter 2521. Control logic 2523 may control the activity of all the circuits on ball 2507, though only a connection to converter 2521 is shown in FIG. 25. Control logic 2523 may be a signal processor which digitizes and formats such signals for transmission as a binary data stream. Where a plurality of ball ICs 2507 are used, the binary data stream can be provided with appropriate protocol information including a unique ID for each ball IC 2507 for use in identifying each ball IC 2507 that is transmitting. This coding is especially advantageous where more than one ball IC 2507 is being monitored.

To transmit information, ball 2507 includes an RF oscillator 2525. The frequency of RF oscillator 2525 is preferably not the same as the frequency generated by RF oscillator 2509 of control unit 2501. The RF signal produced by RF oscillator 2525 is modulated with the signal produced by converter 2521 in an RF modulator 2527. The modulated RF signal is amplified by an RF amplifier 2529, which is coupled to antenna/coil 2505. Ball 2507 may operate under AM, FM, PM, or other analog or digital modulation methods. The information transmitted from ball 2507 is received at antenna/coil 2503 of control unit 2501. The RF signal received at antenna/coil 2503 is detected by an RF detector 2531 and amplified by an RF amplifier 2533. The amplified RF signal is converted to a digital signal by a converter 2535, which is an A/D converter or a demodulator. Converter 2535 is coupled to control logic 2537, which processes the data received from ball 2507, and controls a display 2539 and other electrical circuitry of control unit 2501. Display 2539 is either a display to a human operator or it may be an interface to other equipment.

Figure 26:
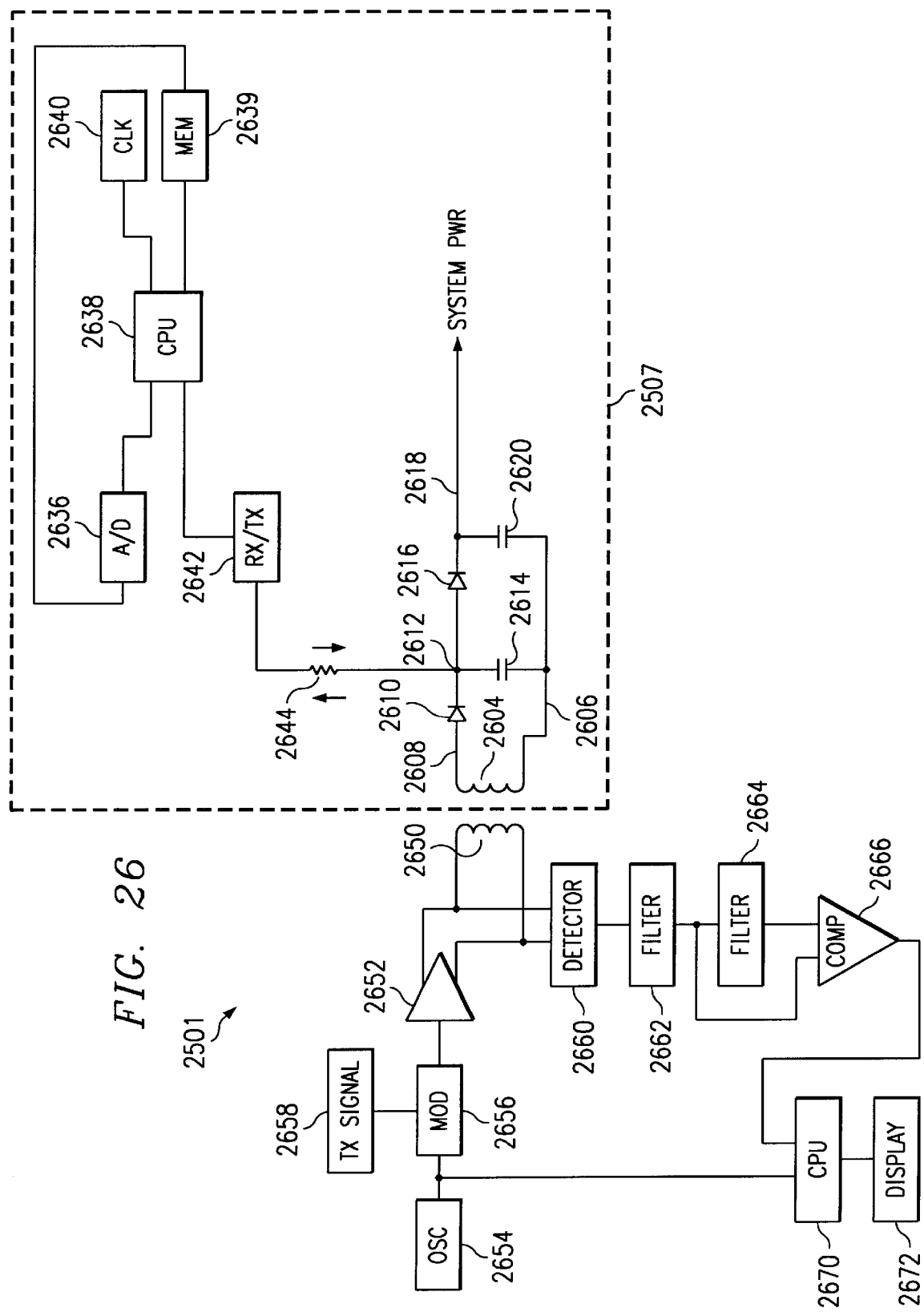
FIG. 26 illustrates a more detailed schematic block diagram of the ball IC in a memory function and the control system, according to a disclosed embodiment.

Referring now to FIG. 26, there is illustrated a more detailed schematic block diagram of the ball IC in a memory function and the control system, according to a disclosed embodiment. The ball 2507, as described hereinabove, is operable to provide unique information according to either its onboard programmed instructions, or to instructions transmitted thereto. The illustrated embodiment of FIG. 26 is that associated with a "passive" system, since it has no battery associated therewith. In order to operate the system, there is provided an inductive coupling element 2604 in the form of an inductor, which is operable to pick up an alternating wave or impulse via inductive coupling, and extract the energy therein for storage in the inductive element 2604. This will create a voltage across the inductive element 2604 between a node 2606 and a node 2608. A diode 2610 is connected between the node 2608 and the node 2612, with the anode of diode 2610 connected to node 2608 and the cathode of diode 2610 connected to a node 2612. Typically, the diode 2610 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 2610 is operable to rectify the voltage across the inductive element 2604 onto the node 2612, which has a capacitor 2614 disposed between node 2612 and node 2606. Node 2612 is also connected through a diode 2616 having the anode thereof connected to node 2612 and the cathode thereof connected to a node 2618 to charge up a capacitor 2620 disposed between node 2618 and 2606. The capacitor 2620 is the power supply capacitor for providing power to the ball 2507. The capacitor 2614, as will be described hereinbelow, is operable to be discharged during operation of the system and, therefore, a separate capacitor, the capacitor 2620, is required for storing power to power the system of the ball 2507.

A CPU 2638 is provided to control and process onboard functions of the ball 2507. A clock circuit 2640 provides timing to the system. A memory 2639 is provided in communication with the CPU 2638 to allow the CPU 2638 to store data therein for later transmittal back to the remote location or for storing received instructions. This memory 2639 can be volatile or it can be non-volatile, such as a ROM, and can be used to store unique information according to its programmed function. For the volatile configuration, of course, this will lose all information when the power is removed. The memory 2639 is also connected to an A/D converter 2636 for conversion of the memory data prior to transmission to the control station 2501, or the memory data may be pulled from the memory 2639 by the CPU 2638 for conversion to the AID converter 2636. System power to all power-consuming elements of the ball 2507 is provided at the SYSTEM PWR output node.

In order to communicate with the CPU 2638 for transferring data thereto and for allowing the CPU 2638 to transfer data therefrom, a receive/transmit circuit 2642 is provided for interfacing to node 2612 through a resistive element 2644. This allows RF energy to be transmitted to node 2612. It is important to note that the semiconductor junction across diode 2610 is a capacitive junction. Therefore, this will allow coupling from node 2612 to node 2608. Although not illustrated, this could actually be a tuned circuit, by selecting the value of the capacitance inherent in the design of the diode 2610. In any event, this allows an RF connection to be provided across diode 2610 while allowing sufficient energy to be input across conductive element 2604 to provide a voltage thereacross for rectification by the diode 2610 and capacitor 2614. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al., U.S. Pat. No. 3,944,982, entitled "Remote Control System For Electric Apparatus," issued Mar. 16, 1976, both of which are referenced hereinabove. With these types of systems, power can be continually provided to the node 2612 and subsequently to capacitor 2620 to allow power to be constantly applied to the ball 2507.

The monitor system 2501 which is disposed outside of the body and proximate to the ball 2507 includes an inductive element 2650 which is operable to be disposed in an area proximate to the skin, yet exterior to the body, in the proximity of the ball 2507. The inductive element 2650 is driven by a driving circuit 2652 which provides a differential output that is driven by an oscillator 2654. This will be at a predetermined frequency and power level necessary to couple energy from inductive element 2650 to inductive element 2604. Since this is an external system, the power of the oscillator can be set to a level to account for any losses through the body tissues. To allow information to be transmitted, a modulation circuit 2656 is provided which is modulated by a transmitter signal in a block 2658 that allows information to be modulated onto the oscillator signal of the oscillator 2654, which oscillator signal is essentially a "carrier" signal. However, it should be understood that the information that is transmitted to the ball 2507 could merely be date information, whereas the CPU 2638 could operate independent of any transmitted information to provide the correct timing for the output pulses and the correct waveshape therefor. Alternatively, entire control of the system could be provided by the transmit signal 2658 and the information carried thereon, since power must be delivered to the illustrated embodiment due to the lack of any independent power in the ball 2507.

When the information is received from the ball 2507, it is superimposed upon the oscillator signal driving the inductive element 2650. This is extracted therefrom via a detector 2660 which has the output thereof input to a first low pass filter 2662, and then to a second low pass filter 2664. The output of low pass filters 2662 and 2664 are compared using a comparator 2666 to provide the data. The filter 2662 provides an average voltage output, whereas the filter 2664 provides the actual digital voltage output. The output of the comparator 2666 is then input to a CPU 2670 which also is powered by the oscillator 2654 to process the data received therefrom. This can then be input to a display 2672 for presentation to an operator or technician.

Other Invasive and Non-Invasive Biomedical Applications

Other applications include monitoring changes in ion concentration, pH, electrical activity (EKG, EEG), levels of glucose, proteins, lipids, carbohydrates, enzymes, hormones, hemoglobin, cell integrins, variations in temperature, pressure, position, velocity, emissions of x-rays, light, sound, infrared, changes in rhythm or frequency, and the like. Sensor 160 is conventional in operation in that it may include sensor functions to measure any physiological condition of interest, and may be fabricated according to the disclosed spherical architecture.

The ball sensor may also be attached or integral with the surfaces of orthopedic instruments to determine distance, force or pressure when a physician is unable to visualize or otherwise sense that parameter, for example in an arthroscopic surgical procedure to reattach ligament to bone. Still further, a position sensor may also be located on scalpel blades or scissors to determine, during orthopedic surgery, the distance of the blades or scissors from another surgical device or instrument also containing appropriate sensors. Thus, the position sensor-containing ball semiconductor can give position location of internal or external body parts through radio frequency communication to an outside central processing unit, but also between an inanimate object (such as suture or scalpel) and an internal vital structure containing a similar position sensing ball. In certain instances where the ball can be inserted onto a catheter, guidewire, needle stylet, that direct electrical connections can be made from the ball to a remote CPU. In this event, communication would be by hardwire as opposed to wireless techniques. In still another embodiment, a ball adapted with both hardwire and wireless links to a remote computer are possible.

Similarly, a bioelectric sensor can be used to detect electrical activity at other points of the body. A ball sensor can be externally attached to a surface of a patient's skin or inserted as part of a microelectrode or even implanted to serve as a monitor of muscle activity (electromyographic monitoring) or nerve activity (nerve conduction velocity) for the diagnosis and evaluation of neuromuscular disorders. Placement of ball semiconductors attached with tissue glue to skeletal, muscular, or connective tissue structures is also feasible.

Many types of sensors are known in the art for measuring numerous types of quantitative conditions. Signals generated by conventional sensors indicative of force, velocity, acceleration, position, or pressure can be processed in accordance with the fabrication architecture disclosed by Applicant in U.S. Pat. No. 5,955,776 entitled "Spherical Shaped Semiconductor Integrated Circuit," which issued Sep. 21, 1999, and which is referenced hereinabove, to produce a signal for transmission from the ball IC to a remote station for external monitoring of physiological conditions. A variety of conventional sensors are provided in, for example, ELECTRONIC ENGINEER'S HANDBOOK, 2nd Edition, Fink Christianson, McGraw Hill (1982), BIOMEDICAL ENGINEERING HANDBOOK, Joseph D. Bronzino, Editor-in-Chief, CRC Press (1995), and other like publications.

It will be appreciated that other modifications of the above are possible without departing from the spirit and scope of the invention. For instance, in yet another embodiment of this invention a ball device is provided with two sensors. These sensors can monitor the same or different physiological activities. If the same physiological activity, such as pressure, is monitored, then ball 110 advantageously allows there to be two pressure readings to be taken for purposes of integrity, redundancy; and/or 3-D pressure monitoring. Integrating and redundancy sensors can derive from locating two or more sensors located anywhere along the surface of the semiconductor ball 110 in a high pressure area of the body where pressure differentials between the two sensors are minimal. Alternatively, if the semiconductor ball 110 is to be used in a low pressure area, the sensors should be located close together on the semiconductor ball so as to minimize pressure differentials between the two sensors.

If a different sensor is used, then ball semiconductor advantageously allows two or more physiological parameters to be monitored by the ball. Because of the greater surface area of the ball when compared to conventional flat IC, the ball advantageously allows for an increased number of sensors to be placed within the same space that would be defined by a conventional flat IC. Placement of the same type of sensors in the ball can allow for increased integrity, redundancy and 3-D monitoring of the orthopedic device or tissue of interest. Placement of different sensors in the ball can allow for more comprehensive monitoring of a wider range of physiological parameters than allowed using conventional flat ICs.

It will also be appreciated that two biomedical balls with one or more sensors each can be clustered together to form a biomedical device that provides expanded three dimensional monitoring. The expanded device of the cluster kind allows for placement of even more sensors at critical locations invasively or non-invasively for increased integrity, redundancy, 3-D monitoring, and/or monitoring of a more comprehensive set of physiological activities.

Diagnostics and Imaging

The main function of diagnostic imaging is to produce images of internal organs of the body for diagnostic purposes. In one technique, x-rays are used to produce shadow images of internal organs of the body. Computer tomography is another x-ray based technique where a narrow x-ray beam is passed through a body at several points along a plane so as to produce an image with some 3-D perception. Ultrasound is yet another imaging system used for diagnoses. Nuclear medicine is also used for imaging. Nuclear medicine involves injection of a radio-labeled substance that is specifically targeted to selectively distribute to specific areas of the body. Magnetic resonance imaging is a recent development in imaging and allows for 3-D perception as well as determining organ function under certain conditions. Conventional imaging radiology is based on these and other imaging techniques.

In one embodiment, magnetic resonance imaging can locate a semiconductor ball without the use of harmful x-rays. This would be very beneficial when located on an orthopedic prosthesis for visualization and location for intricate motions of the skeleton. In addition, no contrast is needed for this visualization decreasing the incidence of allergic reactions and contrast-induced nephrotoxicity. In another embodiment, the use of Doppler imaging via an acoustic emitter and acoustic transmitter present on different semiconductor balls on the same guidewire or catheter would allow for noninvasive imaging of the bone, ligament, tendon or device. The acoustic emitter could also transmit a signal to an external acoustic receiver to allow for dynamic imaging of the object.

The semiconductor ball of this disclosure lends itself readily to 3-D pressure monitoring because of the spherical surface of the ball which allows each sensor to be positioned away from the other so as to be displaced from the other in all three axes. For example, a sensor located at the top of ball 110 and a second sensor located at a midpoint along the surface of the ball 110 could be displaced from each other triaxially (in all three x, y and z axis). This is unlike conventional flat surface IC's where sensors are displaced from each other in only the two dimensions—namely, the x and y axis.

In still another application, the ball is adapted with CCD or digital signal processing optical sensory properties placed at the end of an arthroscope, allowing for 3-D panoramic images without requiring movement of the end of the scope as opposed to the conventional limited planar views obtained with the current flat chip technology, which requires movement of the end of the scope for visualization in other planes of view. The appearance may be similar to that viewed through the eye of a fish. As this is on the end of an arthroscope, it allows for a decrease in the caliber of the instrument, making more sites accessible. The connection to the outside central processing unit may be direct through wire connections inside the arthroscope or via radio frequency conversion. The latter would allow for a further decrease in caliber.

As described hereinabove, the semiconductor ball IC can be introduced either attached to an internal or external orthopedic prosthesis, or alone into bones, joint cavities, intramuscular, and in extracellular fluid compartments for determining force, pressure and acceleration where monitoring of these values may be critical. In another embodiment, a semiconductor ball attached to said devices and tissues, or to a guidewire, stylet, catheter, needle, or introduced alone can be adapted for measuring the same or similar parameters during the intraoperative period when precise manipulation of the tissues of devices are to be accomplished.

From the foregoing disclosure, it can be appreciated that numerous limitations in the prior art can be solved through the use of ball sensors. The fluid column often used in conventional pressure-sensing techniques can be eliminated by communicating with sensors internal to the body. Various catheter and guidewire exchanges would be eliminated thus making the procedure simpler, faster, and safer for the patient and physician. Internal site-specific sensors provide more clear and accurate signals with minimal artifacts for both position registration and functional measurements. Integration of ball sensors along the catheter, guidewire, or other insertable instrument with remote visualization capability allows for magnetic resonance imaging without harmful x-ray exposure for the patient and physician. In a similar manner, a combination of ultrasound emitters and sensors can illicit imaging for accurate positioning without x-ray exposure. Diagnostic and treatment capabilities can be combined on the same catheter, guidewire or insertable instrument. In some cases, external monitor connections are eliminated freeing the patient and caregivers from encumbrances making the entire system more user friendly and simple.

Although the preferred embodiment has been described in detail, it should be understood that various changes, substitutions and alterations can be made therein without departing from the spirit and scope of the invention as defined by the appended claims.

What is claimed is:

1. An implantable integrated circuit for use with implantation in an organic medium associated with an organic organism, comprising:

a substantially spherical shaped substrate;

at least one transducer disposed on said substrate for interacting with the organic medium in which the implantable IC is implanted, said transducer operating in accordance with associated operating parameters; and communications circuitry associated with said substrate for allowing external interface to said at least one transducer for receiving information therefrom, wherein said communications circuitry comprises a wireless communication circuit having an inductive element for receiving external energy for the porpuses of powering said transducer and for communication of information from said at least one transducer external to the implantable integrated circuit.

2. The implantable IC of claim 1, wherein the substrate is comprised of silicon.

3. The implantable IC of claim 2, wherein said at least one transducer is formed within the surface of said silicon substrate.

4. The implantable IC of claim 2, wherein said communications circuitry is formed within said substantially spherical shaped substrate on at least a portion thereof.

5. The implantable integrate circuit of claim 1, wherein said at least one transducer is operable to generate a stimulus to the adjacent organic medium in contact therewith.

6. The implantable integrated circuit of claim 1, wherein said at least one transducer is operable to facilitate stimulating physiological activity.

7. The implantable integrated circuit of claim 1, adapted to an orthopedic implant.

8. An implantable integrated circuit for use with implantation in an implantable orthopedic prostheses, comprising:

a substantially spherical shaped substrate;

at least one transducer disposed on said substrate for interacting with the implantable orthopedic prostheses in which the implantable IC is implanted, said transducer operating in accordance with associated operating parameters; and communications circuitry associated with said substrate for allowing external interface to said at least one transducer for receiving information therefrom.

9. The integrated circuit of claim 8, herein said orthopedic prostheses is an artificial joint.

10. The integrated circuit of claim 8, wherein said orthopedic prostheses is an artificial intervertebral disk.

11. A method for measuring strain in an orthopedic application within a human body, comprising the steps of:

providing a substantially spherical semiconductor substrate having a sensor and integrated circuitry formed thereon, the integrated circuitry including circuitry connected to the sensor and including communication circuitry for communicating external to the body;

implanting the substantially spherical substrate in an orthopedic medium in the body in such a manner that it can interact with the orthopedic medium through the associated sensor;

measuring strain in the orthopedic medium;

converting the strain measured by the sensor to electrical data; and communicating with the integrated circuitry from external to the body for controlling the operation of the integrated circuitry and extracting the electrical strain data.

12. The method of claim 11, wherein the orthopedic medium in the step of implanting is an implantable orthopedic prostheses.

13. The method of claim 11, wherein the orthopedic medium in the step of implanting is a tendon.

14. The method of claim 11, wherein the orthopedic medium in the step of implanting is a ligament.

15. The method of claim 11, wherein the orthopedic medium in the step of implanting is a bone.

16. The method of claim 15, wherein the orthopedic medium in the step of implanting is a segment of the bone.

* * * * *